(12) United States Patent
Chatlynne et al.

(10) Patent No.: US 7,371,244 B2
(45) Date of Patent: May 13, 2008

(54) DEPLOYMENT APPARATUS FOR SUTURE ANCHORING DEVICE

(75) Inventors: Etan S. Chatlynne, Brooklyn, NY (US); John Collier, Franklin Lakes, NJ (US); Robert Nering, Sergeantsville, NJ (US); John Crombie, East Hanover, NJ (US); Larry Crainich, Charlestown, NH (US)

(73) Assignee: Ethicon, Inc., Somerville, NJ (US)

( * ) Notice: Subject to any disclaimer, the term of this patent is extended or adjusted under 35 U.S.C. 154(b) by 637 days.

(21) Appl. No.: 10/648,494

(22) Filed: Aug. 25, 2003

(65) Prior Publication Data
US 2005/0049617 A1    Mar. 3, 2005

(51) Int. Cl.
*A61B 17/04*    (2006.01)

(52) U.S. Cl. .................. 606/148; 606/139; 606/232

(58) Field of Classification Search ........ 606/144–148, 606/139, 232; 29/270, 272, 280; 411/16, 411/17
See application file for complete search history.

(56) References Cited

U.S. PATENT DOCUMENTS

| | | | |
|---|---|---|---|
| 4,901,721 A | 2/1990 | Hakki | |
| 5,078,731 A | 1/1992 | Hayhurst | |
| 5,123,914 A | 6/1992 | Cope | |
| 5,219,359 A | 6/1993 | McQuilkim et al. | |
| 5,232,204 A * | 8/1993 | Nunez .................... | 254/133 A |
| 5,269,791 A * | 12/1993 | Mayzels et al. ............ | 606/148 |
| 5,376,101 A | 12/1994 | Green et al. | |
| 5,383,905 A | 1/1995 | Golds et al. | |
| 5,391,173 A | 2/1995 | Wilk | |
| 5,409,499 A | 4/1995 | Yi | |
| 5,474,572 A | 12/1995 | Hayhurst | |
| 5,514,159 A | 5/1996 | Matula et al. | |
| 5,520,702 A | 5/1996 | Sauer et al. | |
| 5,537,776 A | 7/1996 | Gilard, Sr. | |
| 5,630,824 A | 5/1997 | Hart | |
| 5,643,295 A | 7/1997 | Yoon | |
| 5,645,553 A | 7/1997 | Kolesa et al. | |
| 5,662,683 A * | 9/1997 | Kay .......................... | 606/232 |
| 5,681,351 A | 10/1997 | Jamiolkowski et al. | |
| 5,728,116 A | 3/1998 | Rosenman | |
| 5,741,301 A | 4/1998 | Pagedas | |
| 5,810,853 A | 9/1998 | Yoon | |
| 5,810,882 A | 9/1998 | Bolduc et al. | |
| 5,820,631 A * | 10/1998 | Nobles ...................... | 606/213 |
| 5,824,008 A * | 10/1998 | Bolduc et al. ............. | 606/143 |
| 5,849,019 A | 12/1998 | Yoon | |
| 5,919,208 A | 7/1999 | Valenti | |

(Continued)

FOREIGN PATENT DOCUMENTS

EP    0 663 184 A1    7/1995

(Continued)

*Primary Examiner*—Glenn K. Dawson
*Assistant Examiner*—Kathleen Sonnett

(57) ABSTRACT

A deployment device for anchoring a suture to a suture anchoring device, which is made from a helically coiled member, includes a winding tube for winding a suture around the coiled member in a helical path such that the suture is attached to at least one turn of the coiled member. A support mechanism is also provided for supporting the suture anchoring device during the winding of the suture around the coiled member. The deployment device can be used for anchoring a string and the like to any helically coiled member.

37 Claims, 21 Drawing Sheets

U.S. PATENT DOCUMENTS

| | | |
|---|---|---|
| 5,976,159 A | 11/1999 | Bolduc et al. |
| 6,001,110 A | 12/1999 | Adams |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,099,553 A | 8/2000 | Hart et al. |
| 6,106,545 A | 8/2000 | Egan |
| 6,126,677 A | 10/2000 | Ganaja et al. |
| RE36,974 E | 11/2000 | Bonutti |
| 6,165,204 A | 12/2000 | Levinson et al. |
| 6,200,329 B1 | 3/2001 | Fung et al. |
| 6,231,592 B1 | 5/2001 | Bonutti et al. |
| 6,293,961 B2 | 9/2001 | Schwartz et al. |
| 6,409,743 B1 | 6/2002 | Fenton, Jr. |
| 6,428,550 B1 | 8/2002 | Vargas et al. |
| 6,517,578 B2 | 2/2003 | Hein |
| 6,599,311 B1 * | 7/2003 | Biggs et al. .................. 606/232 |
| 6,626,917 B1 * | 9/2003 | Craig .......................... 606/144 |
| 6,652,562 B2 | 11/2003 | Collier et al. |
| 2003/0195562 A1 * | 10/2003 | Collier et al. ................ 606/232 |

FOREIGN PATENT DOCUMENTS

| | | | |
|---|---|---|---|
| WO | WO-00/28902 | * 11/1998 | .................. 606/143 |
| WO | WO 99/62406 A2 | 12/1999 | |
| WO | WO 00/28902 A1 | 5/2000 | |
| WO | WO 01/45570 A1 | 6/2001 | |
| WO | WO 01/45571 A1 | 6/2001 | |

\* cited by examiner

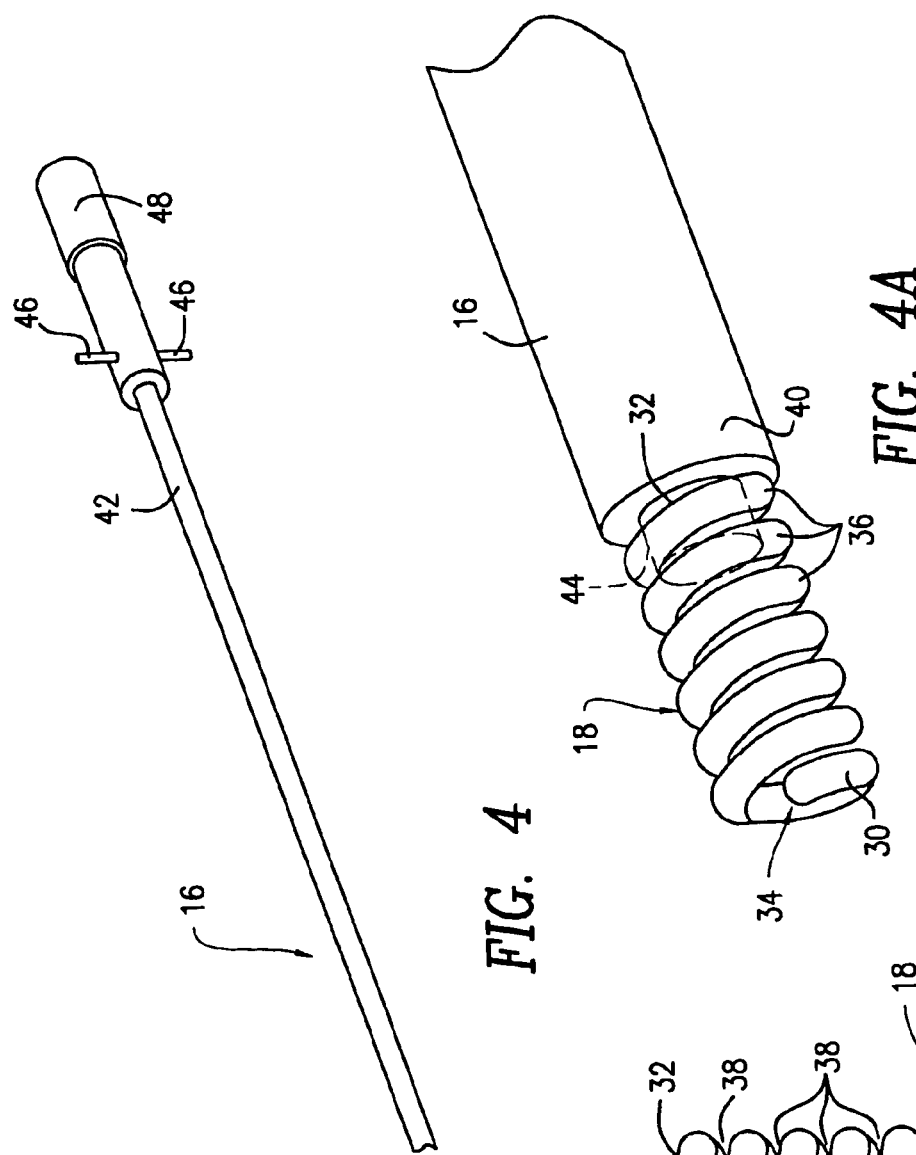
FIG. 4
FIG. 4A
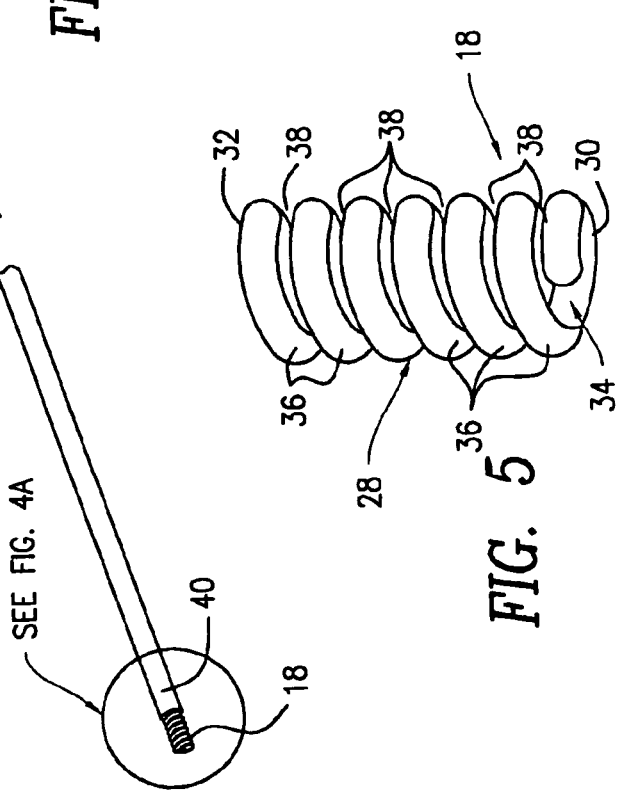
FIG. 5

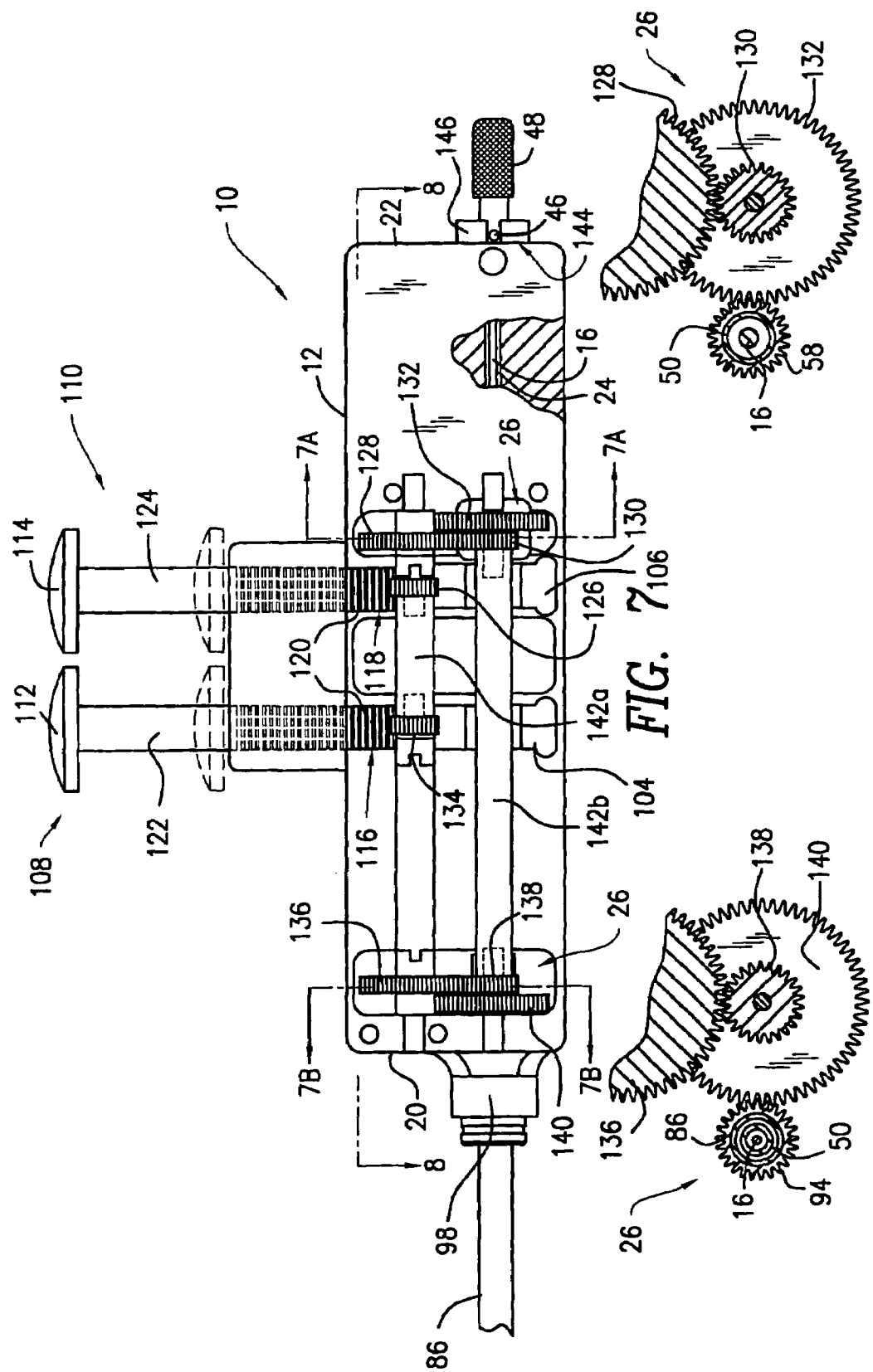

DEPLOYMENT APPARATUS FOR SUTURE ANCHORING DEVICE

FIELD OF THE INVENTION

The present invention relates to apparatus for deploying a suture anchoring device at a wound or surgical site and, more particularly, to apparatus for securing a suture to a suture anchoring device.

BACKGROUND OF THE INVENTION

In surgical procedures, sutures are commonly used to close incisions and to reunite damaged tissue. Typically, the sutures are maneuvered and passed through the affected tissue and the free ends of the sutures are individually tied together by the surgeon. In most surgical incisions, the surgical site area is sufficiently exposed to permit the surgeon to access and quickly tie the suture manually with a surgical knot. However, in other surgical procedures, such as endoscopic procedures, laparoscopic procedures, arthroscopic procedures and the like, or when robotic surgical procedures occur, the suturing site is inaccessible to the surgeon's hands. As a result, the surgeon needs to tie each of the suture ends into a knot at a location remote from the suturing site, and then manipulate suitably configured instruments for sliding the surgical knot to the suturing site of the incision. Further, surgeons may tie surgical knots intracorporeally (inside of the body) using surgical tools to tie the knot down to the tissue. Conventionally, most surgical sutures are secured with surgical knots that are somewhat cumbersome and slow to tie. As a result, knot tying is one of the more time-consuming steps in the suturing process of the surgical procedure. Also, it is noted that knots are weak points in a suture. That is to say, when a knotted suture is broken from applied tension (assuming the suture is otherwise free from imperfections), the suture will break at the knot.

Co-pending, commonly owned U.S. patent application Ser. No. 10/122,970 filed Apr. 12, 2002 discloses a suture anchoring device addressing the problems discussed above. More particularly, the suture anchoring device is made from a coiled member having a helical configuration with a multiplicity of turns. When used in connection with a surgical procedure, the suture anchoring device is positioned adjacent to a wound site and a suture is attached to at least two of the turns so as to anchor the suture to the coiled member.

Various tools have been developed in the past for facilitating the attachment of sutures to securing mechanisms, such as clips, retainers, etc. (see, for instance, U.S. Pat. Nos. 5,520,702, 6,099,553 and 6,231,592). However, these tools are not adapted for use in anchoring a suture to the suture anchoring device disclosed in the '970 Application discussed above. Accordingly, there is a need for a tool for deploying such a device at a wound site.

SUMMARY OF THE INVENTION

The present invention overcomes the disadvantages and shortcomings of the prior art discussed above by providing a new and improved deployment apparatus adapted for use in anchoring a suture to a suture anchoring device which includes a coiled member having a helical configuration. More particularly, the deployment apparatus includes a winding mechanism for winding the suture about the coiled member such that the suture is attached to at least one turn of the coiled member. The deployment apparatus also includes a supporting mechanism for supporting the coiled member during the winding of the suture about the coiled member. The deployment apparatus can be adapted for use in a non-medical procedure for anchoring a string and the like to any coiled member having a helical configuration.

BRIEF DESCRIPTION OF THE DRAWINGS

For a more complete understanding of the present invention, reference is made to the following detailed description of exemplary embodiments considered in conjunction with the accompanying drawings, in which:

FIG. 4 is a perspective view of a support rod utilized in the suture winding device shown in FIG. 1;

FIG. 4A is an enlarged perspective view of a distal end of the support rod shown in FIG. 4, a suture anchoring device being attached to the distal end of the support rod;

FIG. 5 is a perspective view of the suture anchoring device shown in FIG. 4A;

FIG. 7 is a cross-sectional view, taken along section line 7-7 and looking in the direction of the arrows, of the suture winding device shown in FIG. 1;

FIG. 7A is a cross-sectional view, taken along section line 7A-7A and looking in the direction of the arrows, of a set of gears mounted in a casing of the suture winding device shown in FIG. 7;

FIG. 7B is a cross-sectional view, taken along section line 7B-7B and looking in the direction of the arrows, of another set of gears mounted in the casing of the suture winding device shown in FIG. 7;

DETAILED DESCRIPTION OF THE PREFERRED EMBODIMENTS

Figure 1:
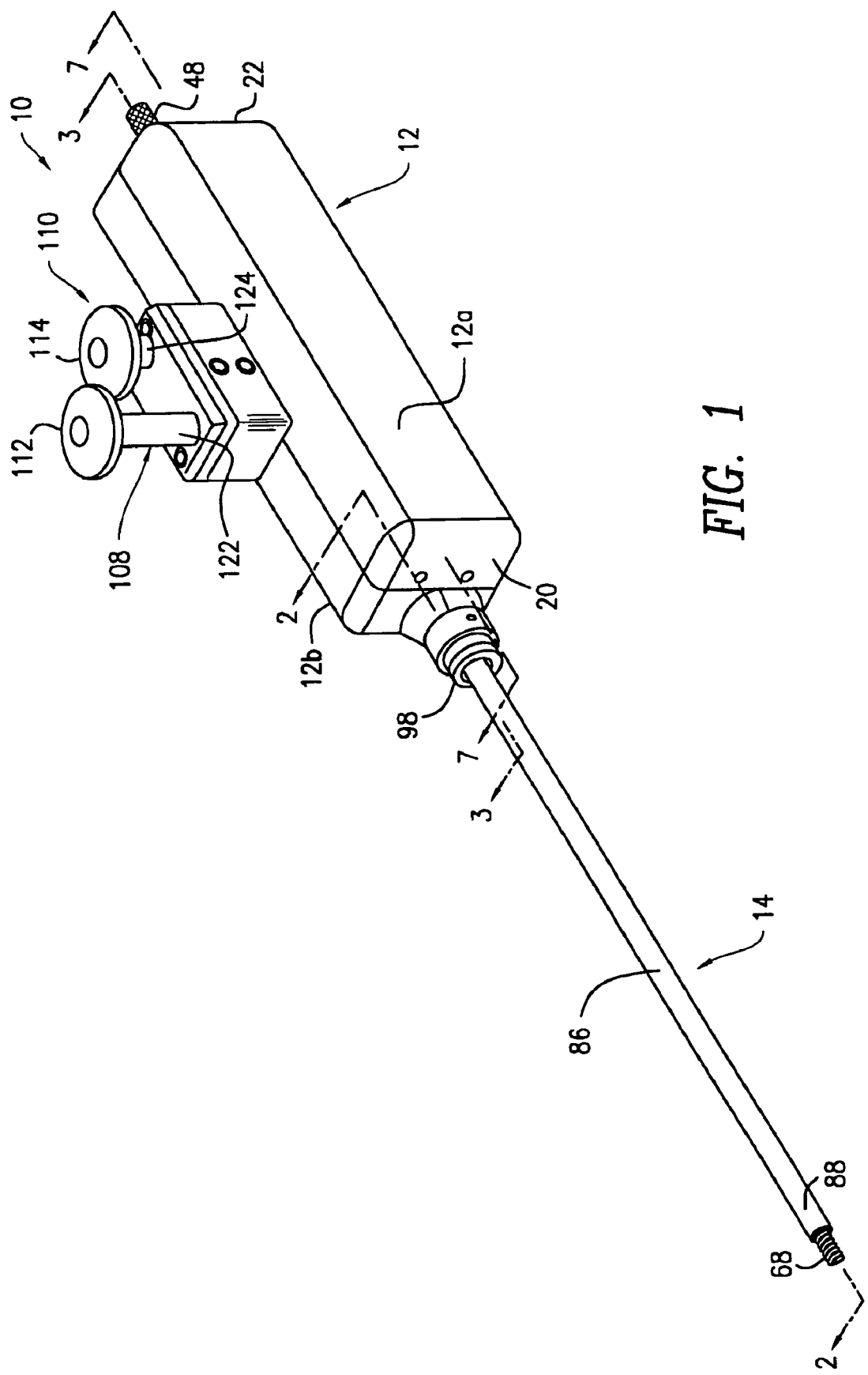
FIG. 1 is a perspective view of a suture winding device constructed in accordance with a first embodiment of the present invention.

FIG. 1 shows a suture winding device 10 constructed in accordance with a first embodiment of the present invention. The suture winding device 10 has a casing or housing 12, a winding tube assembly 14, which projects from the casing 12, and a support rod 16 (see FIGS. 2-4), which extends through the casing 12 and the winding tube assembly 14. The support rod 16 (see FIG. 4) is sized and shaped so as to removably support a suture anchoring device 18 thereon (see FIGS. 4 and 4A). The winding tube assembly 14 is adapted for anchoring or securing a suture to the suture anchoring device 18 in a substantially automatic manner. The casing 12, which has a distal end 20, a proximal end 22 and an internal bore 24 (see FIGS. 2 and 3) extending therethrough between the distal end 20 and the proximal end 22, includes a gear assembly 26 (see FIGS. 7 and 8) for actuating various components of the winding tube assembly 14 during the performance of the suture anchoring operation (i.e., the anchoring of a suture to the suture anchoring device 18). The construction and operation of the casing 12, the winding tube assembly 14, the support rod 16 and the suture anchoring device 18 will be discussed in detail hereinafter.

The suture anchoring device 18 is basically identical, in construction and operation, to the suture anchoring device disclosed in co-pending, commonly owned U.S. patent application Ser. No. 10/122,970, the disclosure of which is incorporated herein by reference. With reference to FIG. 5, the suture anchoring device 18 includes a coiled, circularly-shaped, thin rod or member 28 having a distal end 30 and a proximal end 32 and forming a central opening 34. The suture anchoring device 18 is in its normally coiled helical configuration, wherein its coiled helical rod or member 28 includes a plurality of helically-configured coiled turns or convolutions 36. Due to the coiled helical configuration of the coiled helical rod or member 28, a lateral opening 38 is formed between each adjacent pair of the helically coiled turns 36. Each of the lateral openings 38 can be provided with a dimension (i.e., a distance between each adjacent pair of the helically coiled turns 36) that is approximately equal to the thickness or diameter of a suture to be secured to the suture anchoring device 18. Preferably, the lateral openings 38 can also be provided with a dimension that is about $1/10^{th}$ to $1/4^{th}$ of the thickness or diameter of such a suture.

As used herein, the term "coiled helical configuration" or "coiled spiral configuration" shall define any spiral configuration having a plurality of descending turns, regardless of its geometrical or non-geometrical shape. A geometrical shape is any shape which is conducive to a description using conventional geometry nomenclature. Examples of suitable geometrical shapes include, but are not limited to, the following: circular, oval, elliptical, conical, rectangular, square, triangular, pyramidal and any other polygonal shape. A non-geometrical shape is any shape which is not conducive to a description using conventional geometry nomenclature. Examples of suitable non-geometrical shapes include, but are not limited to, the following: U-shaped, V-shaped, parabolically-shaped and the like.

Still referring to FIG. 5, the suture anchoring device 18 preferably has a height (i.e., a distance measured between the distal end 30 and the proximal end 32) that is equal to about $3/8^{th}$ of an inch. The diameter of the coiled helical rod or member 28 in its non-coiled formation preferably ranges from about 0.012 inch to about 0.020 inch, while the diameter of the central opening 34 is about 0.03 inch. In addition, the suture anchoring device 18 preferably has about five and a half or more helically coiled turns. The suture anchoring device 18 can be provided with different sizes and shapes and a different number of helically coiled turns as disclosed in the '970 Application, depending upon the type of medical procedure for which the suture anchoring device 18 is used.

Referring now to FIGS. 2-4A, the support rod 16 has a distal end 40 and a proximal end 42. The distal end 40 of the support rod 16 has a mounting tip 44 sized and shaped so as to be inserted into the central opening 34 (see FIG. 5) of the suture anchoring device 18 through the proximal end 32. The mounting tip 44 is sized and shaped such that, when inserted into the proximal end 32 of the suture anchoring device 18, it is wrapped around and gripped by at least one helically coiled turn 36 of the suture anchoring device 18. In this manner, a friction fit is formed between the mounting tip 44 and the suture anchoring device 18 such that the suture anchoring device 18 is securely and removably mounted to the support rod 16. When mounted to the support rod 16, the suture anchoring device 18 preferably has four or more turns extending from the mounting tip 44 of the support rod 16. The support rod 16 is also provided with a pair of pins 46 extending radially outwardly therefrom and positioned adjacent the proximal end 42. The proximal end 42 is also provided with a gripping area 48 which is adapted to be gripped by a surgeon's hand.

Figure 2:
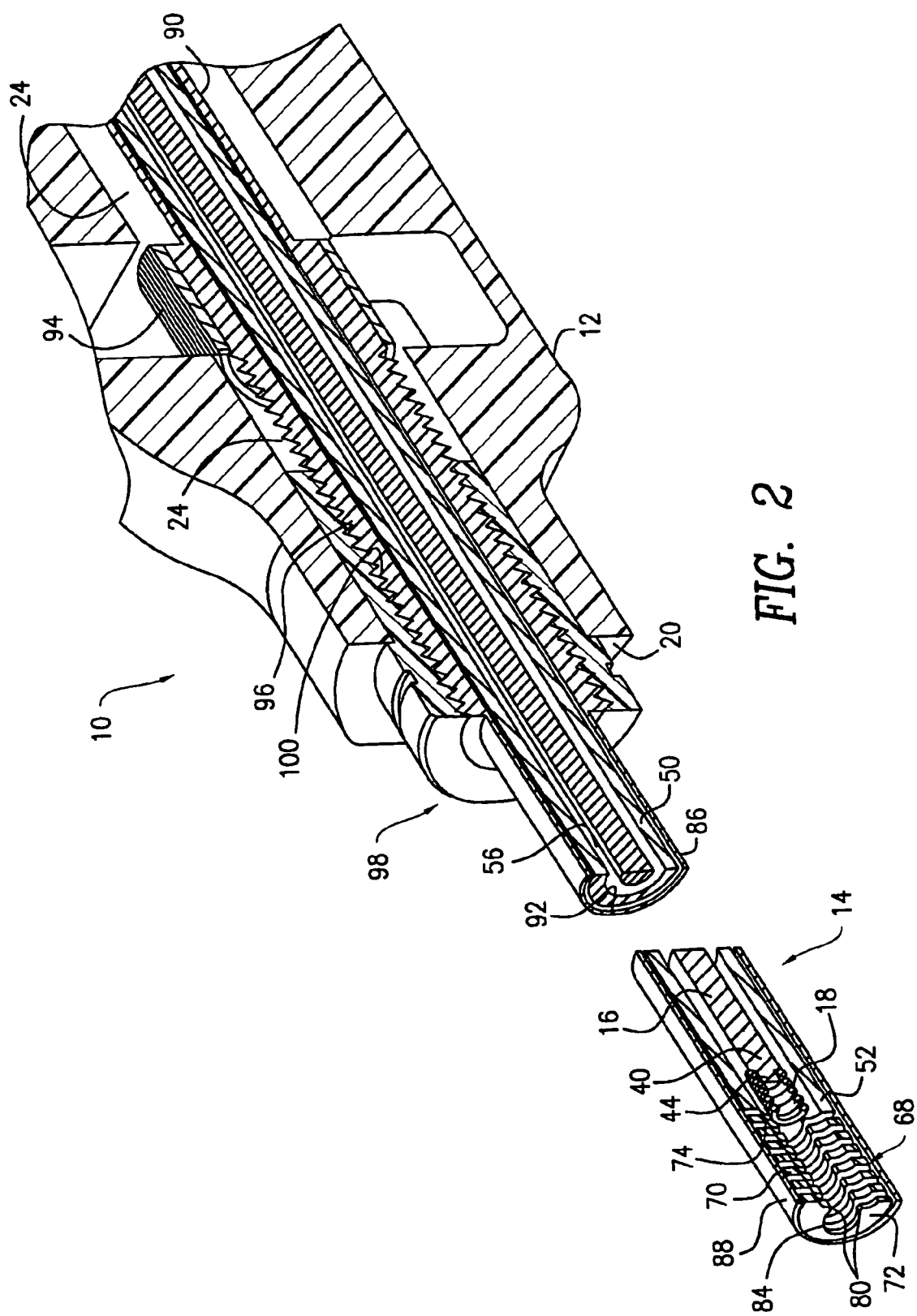
FIG. 2 is a cross-sectional view, taken along section line 2-2 and looking in the direction of the arrows, of the suture winding device shown in FIG. 1.
Figure 3:
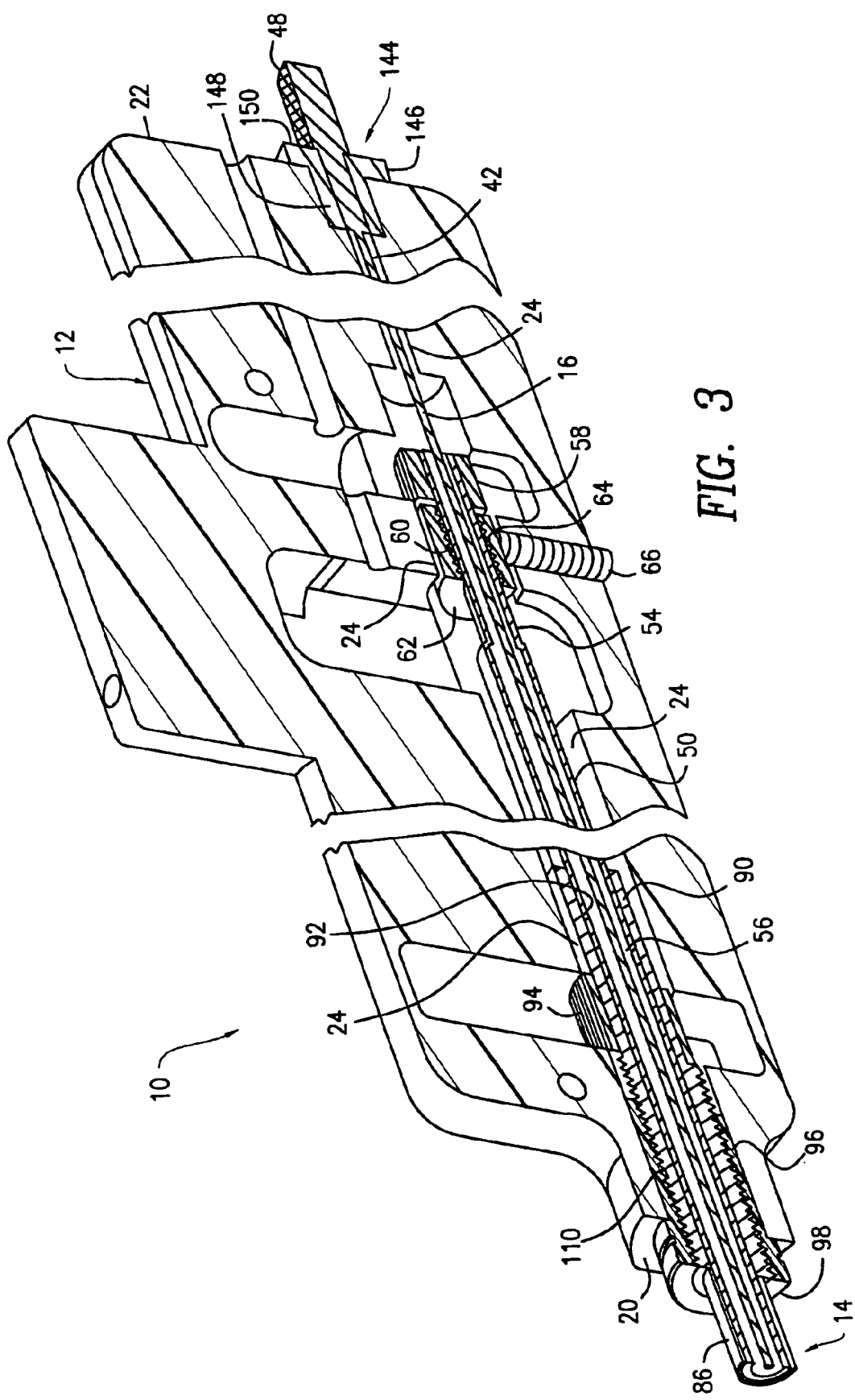
FIG. 3 is a cross-sectional view, taken along section line 3-3 and looking in the direction of the arrows, of the suture winding device shown in FIG. 1.

With reference to FIGS. 2 and 3, the winding tube assembly 14 includes a pilot guide tube 50 projecting from the distal end 20 of the casing 12 and terminating at a distal end 52 thereof. The pilot guide tube 50 also extends into the casing 12 through the bore 24, terminating at a proximal end 54 within the casing 12. A bore 56 extends completely through the pilot guide tube 50 between the distal end 52 and the proximal end 54 thereof. The support rod 16 is sized and shaped so as to extend through the bore 56 of the pilot guide tube 50. The pilot guide tube 50, which is substantially linear, can be made from any suitable materials (e.g., stainless steel).

Figure 8:
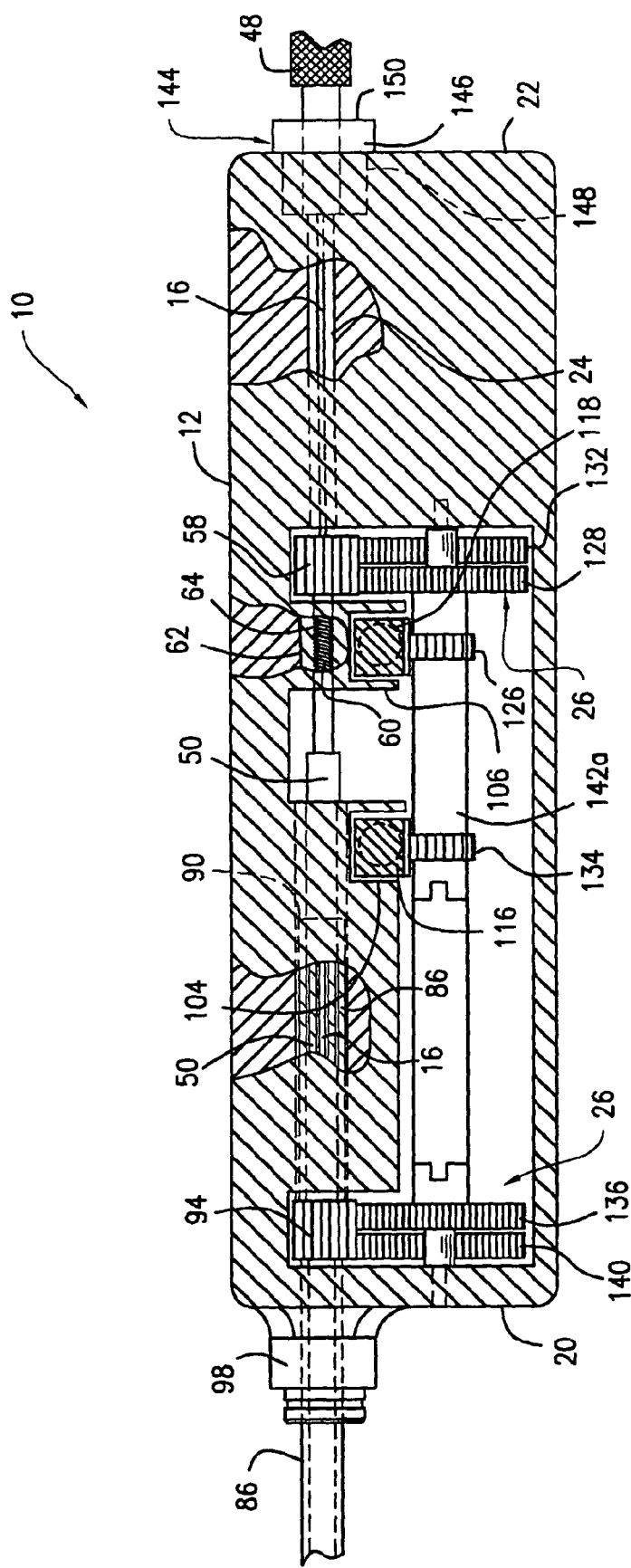
FIG. 8 is a cross-sectional view, taken along section line 8-8 and looking in the direction of the arrows, of the suture winding device shown in FIG. 7.

Now referring to FIGS. 3, 7 and 8, a gear 58 is fixedly mounted on or to the pilot guide tube 50 and positioned in the bore 24 of the casing 12 adjacent the proximal end 54 of the pilot guide tube 50. The gear 58 is adapted to engage the gear assembly 26 of the casing 12 so as to rotate the pilot guide tube 50 in a clockwise or counterclockwise direction relative to the casing 12 as will be discussed in greater detail hereinafter. The pilot guide tube 50 is also provided with screw threads 60 formed thereon adjacent the gear 58. A bushing 62 is mounted in the bore 24 of the casing 12 for rotatably supporting the pilot guide tube 50 in the casing 12. The bushing 62, which has internal screw threads 64, is affixed to the casing 12 by a mounting screw 66 such that it is not movable relative to the casing 12. The pilot guide tube 50 extends through the bushing 62 such that the screw threads 60 of the pilot guide tube 50 are in constant engagement with the screw threads 64 of the bushing 62. In this manner, when the gear 58 of the pilot guide tube 50 is rotated by the gear assembly 26 of the casing 12, the screw threads 60 of the pilot guide tube 50 mate with the screw threads 64 of the bushing 62 for causing the pilot guide tube 50 to move in an axial direction (i.e., in a direction substantially parallel to the longitudinal axis of the casing 12 or the pilot guide tube 50) relative to the casing 12. In other words, the pilot guide tube 50 is adapted to move in the axial direction in response to its rotational movement.

Figure 6:
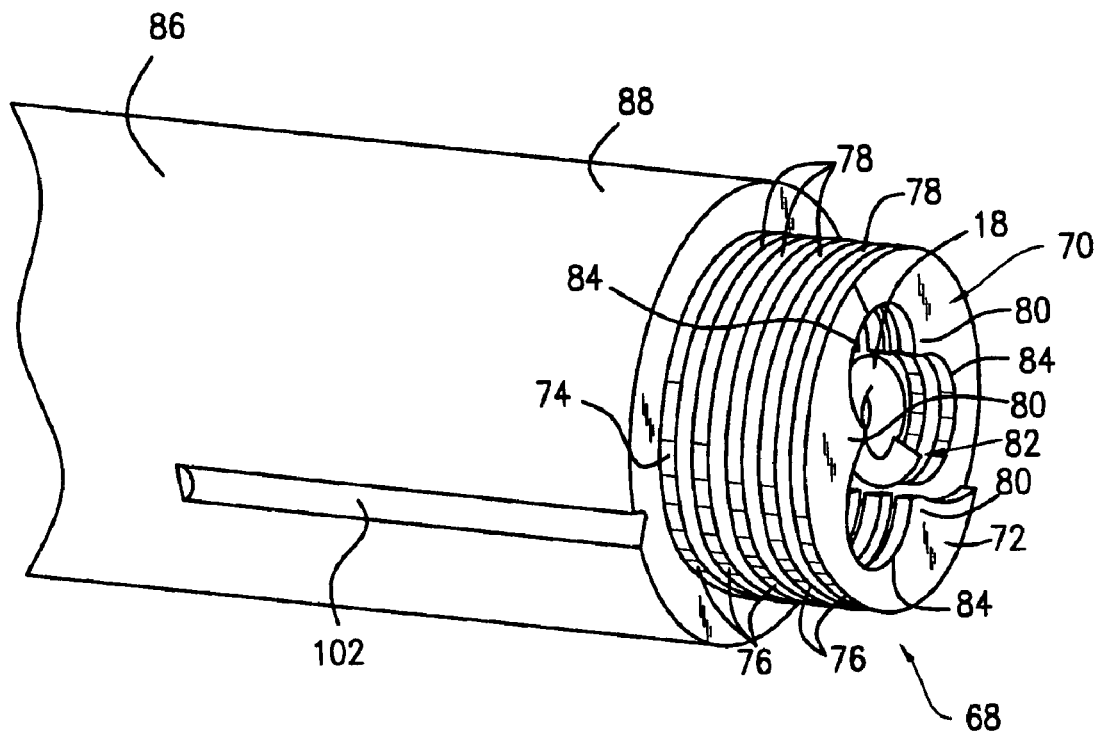
FIG. 6 is a perspective view of a distal end of a winding tube assembly of the suture winding device shown in FIG. 1.

With reference to FIGS. 1, 2, 6 and 6A, the distal end 52 of the pilot guide tube 50 includes a helical pilot guide 68. More particularly, the helical pilot guide 68 includes a coiled, circularly-shaped, thin member 70 having a distal end 72 and a proximal end 74. As shown in FIG. 6, the helical pilot guide 68 is in its coiled helical or spiral configuration, wherein its coiled helical or spiral member 70 includes a plurality of helically configured, coiled turns or convolutions 76. Due to the helical configuration of the helical pilot guide 68, a lateral opening 78 is formed between each adjacent pair of the helically coiled turns 76.

Figure 6A:
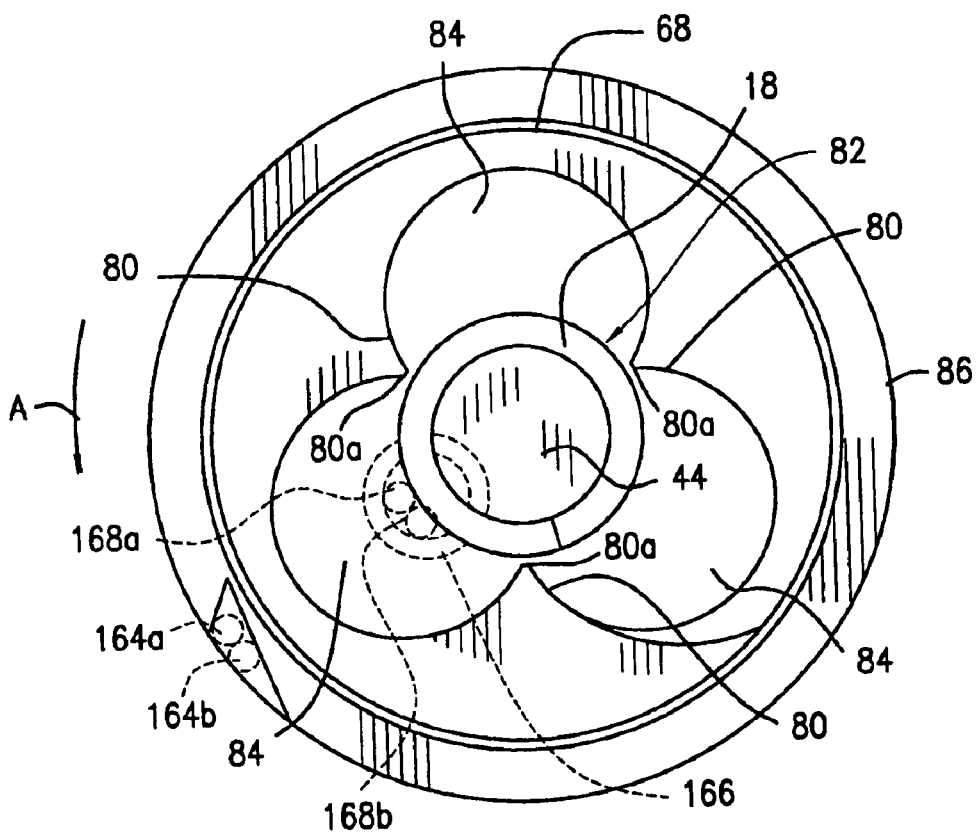
FIG. 6A is a front elevational view of the distal end of the winding tube assembly shown in FIG. 6.
Figure 10A:
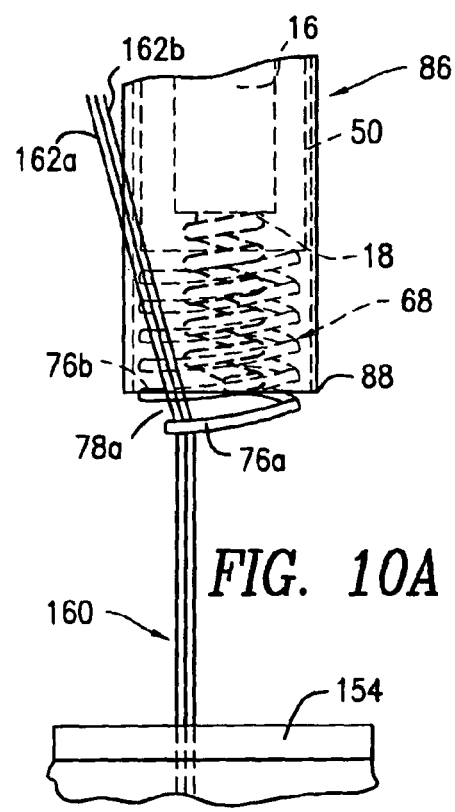
FIGS. 10A-10G are schematic views of the winding tube assembly of the suture winding device shown in FIG. 1, illustrating its suture-anchoring steps.
Figure 10B:
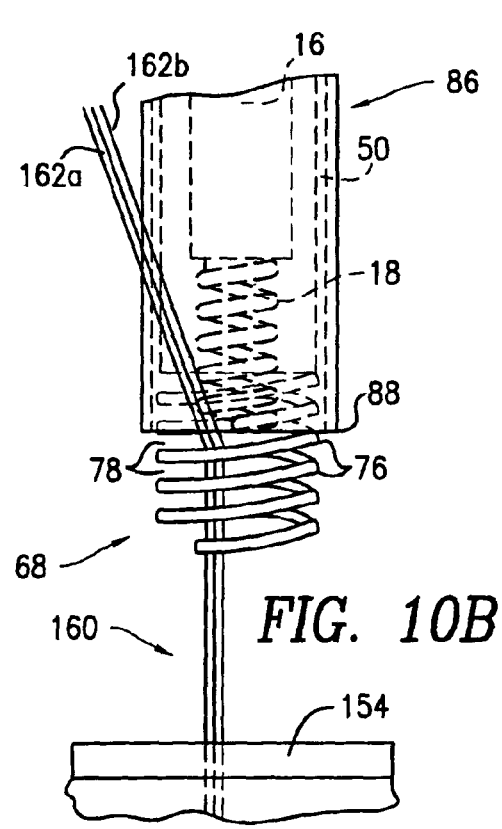
Figure 10C:
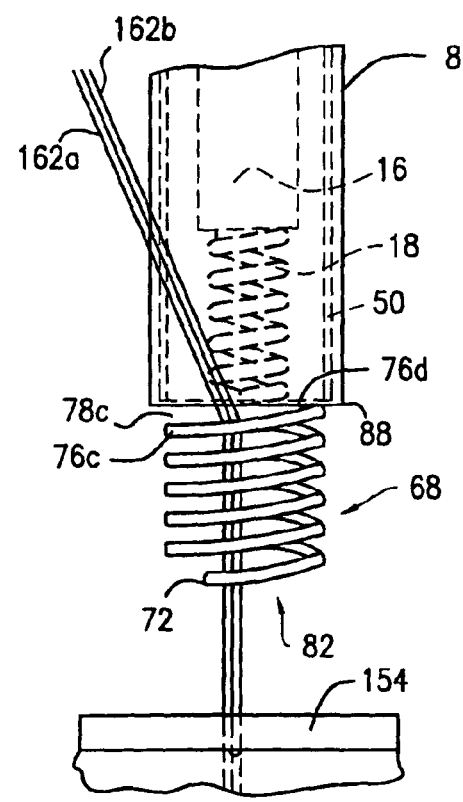
Figure 10D:
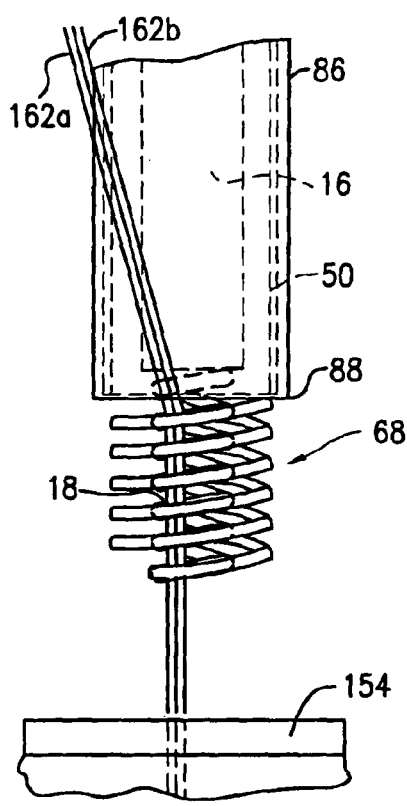

Now referring primarily to FIGS. 2, 6 and 6A, the bore 56 of the pilot guide tube 50 extends completely through the helical pilot guide 68, which has an axial length sufficient to accommodate the suture anchoring device 18 therewithin (see also FIGS. 10A and 10D). Each of the helically coiled turns 76 of the helical pilot guide 68 has a plurality of lobes 80 extending radially inwardly so as to define a central opening 82 extending axially through the helical pilot guide 68. A partially circular space 84 is also formed between each adjacent pair of the lobes 80. The circular spaces 84 of each helically coiled turn 76 of the helical pilot guide 68 radially surround the central opening 82. The central opening 82 is adapted to receive the suture anchoring device 18 (see FIGS. 6 and 6A) during the performance of the suture anchoring operation as will be discussed in greater detail hereinafter. When the suture anchoring device 18 is properly positioned in the central opening 82, it is radially surrounded by the lobes 80 (see FIG. 6A). In this regard, each of the lobes 80 is provided with a size sufficient to support and to thereby stabilize the suture anchoring device 18 within the central opening 84 during the winding of a suture about the suture anchoring device 18. More particularly, the lobes 80 are sized and shaped such that each of their tips 80a terminates immediately adjacent the suture anchoring device 18 positioned in the central opening 82. The lobes 80 are also provided with rigidity greater than the rigidity of the suture anchoring device 18. In this manner, the suture anchoring device 18, which is subjected to lateral (i.e., radial) stresses during the winding of a suture thereabout, is inhibited from deflecting laterally (i.e., in a radial direction), thereby facilitating the proper anchoring of the suture to the suture anchoring device 18.

Figure 11A:
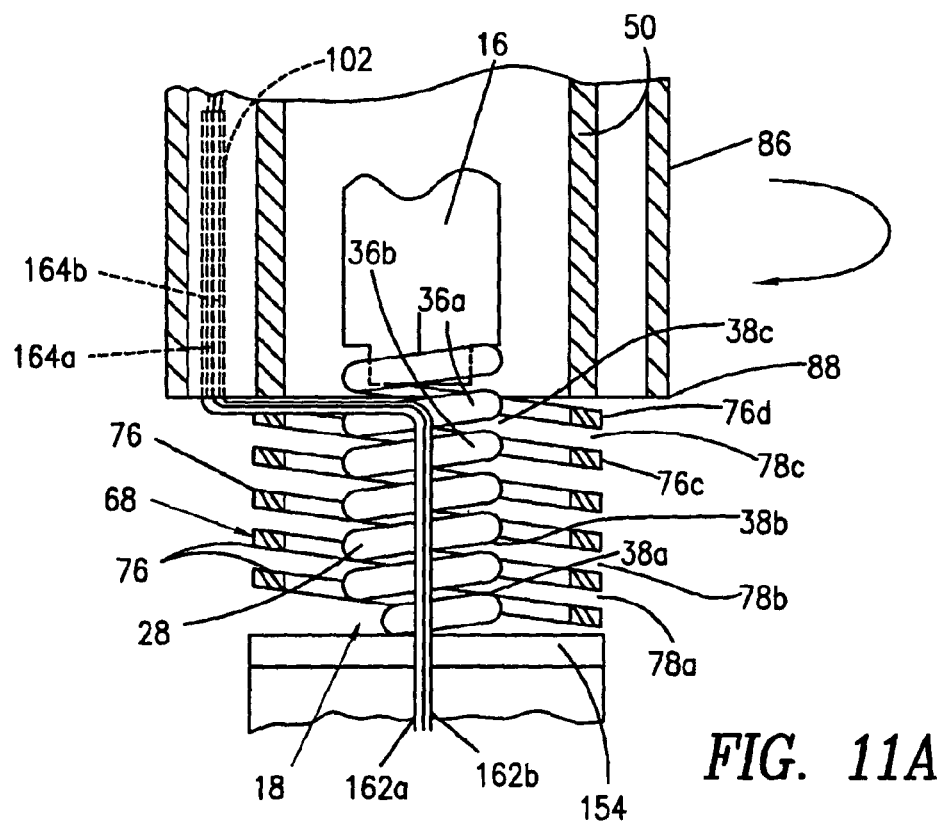
FIGS. 11A-11F are schematic views of the winding tube assembly of the suture winding device shown in FIG. 1, illustrating its suture-winding steps, the front portion of the winding tube assembly being broken away to show the suture anchoring device.
Figure 11B:
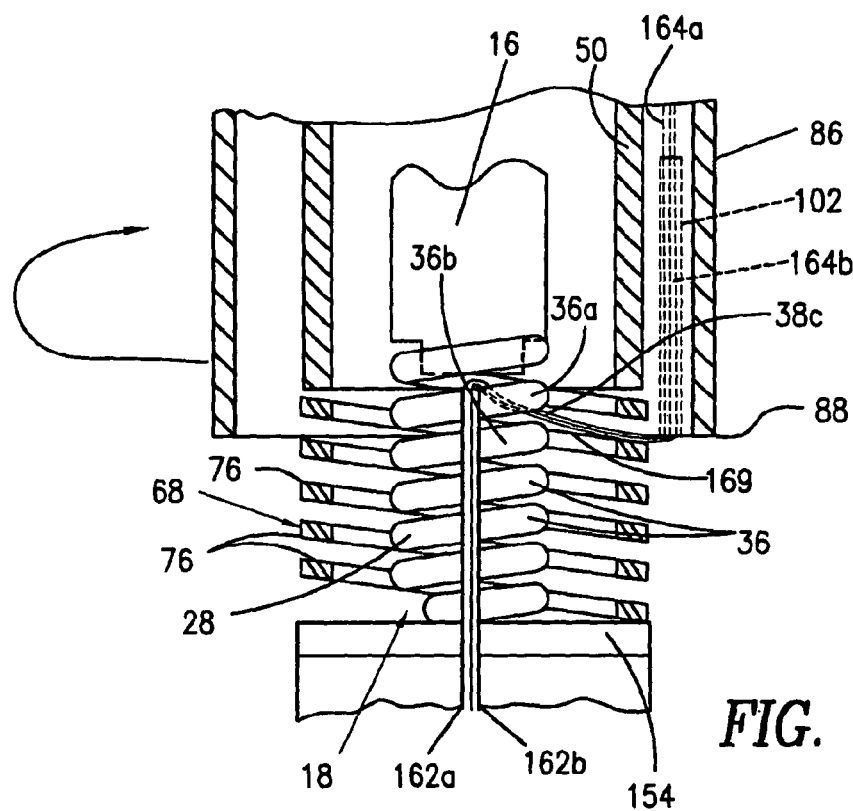
Figure 11C:
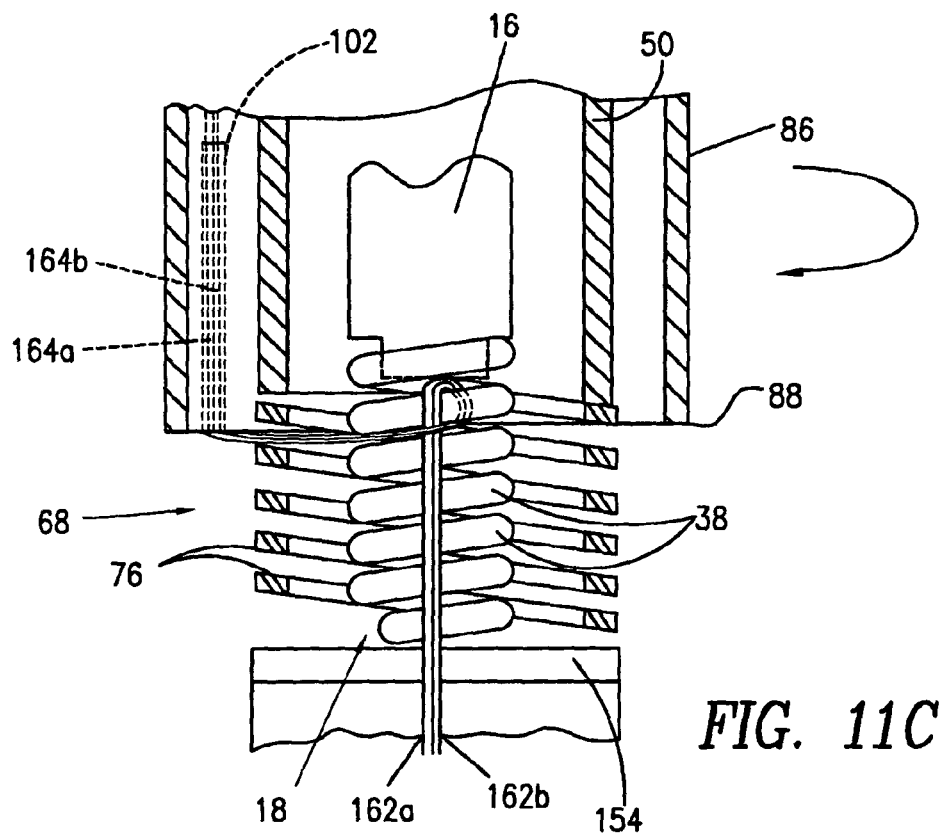
Figure 11D:
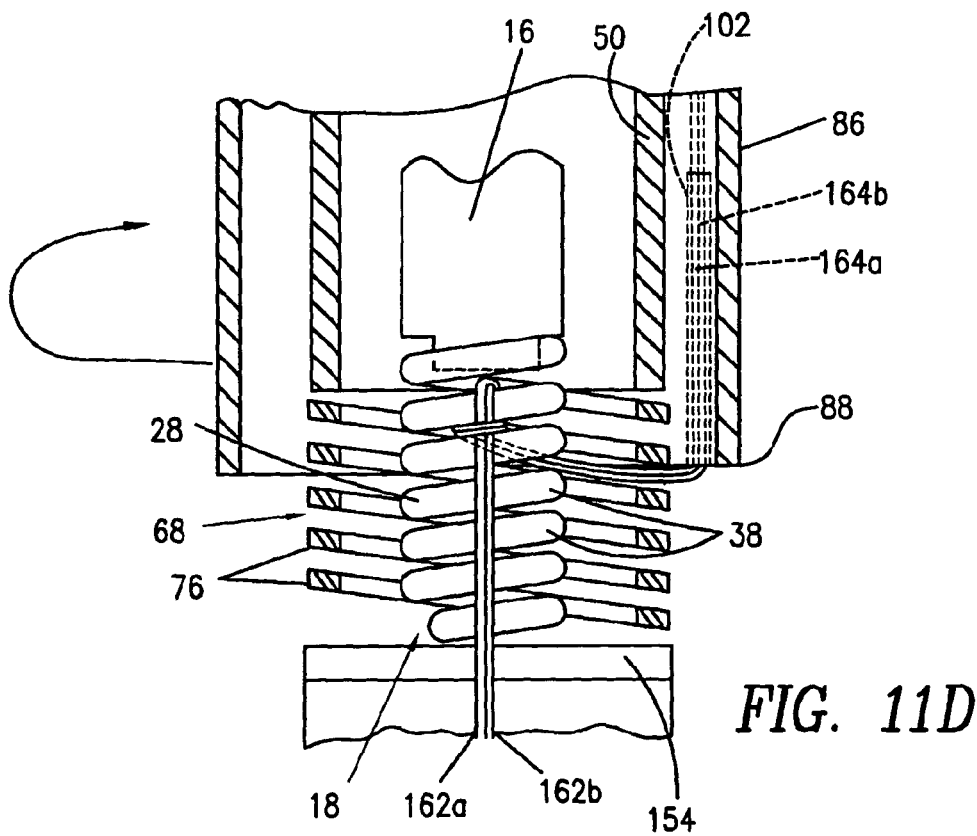
Figure 11E:
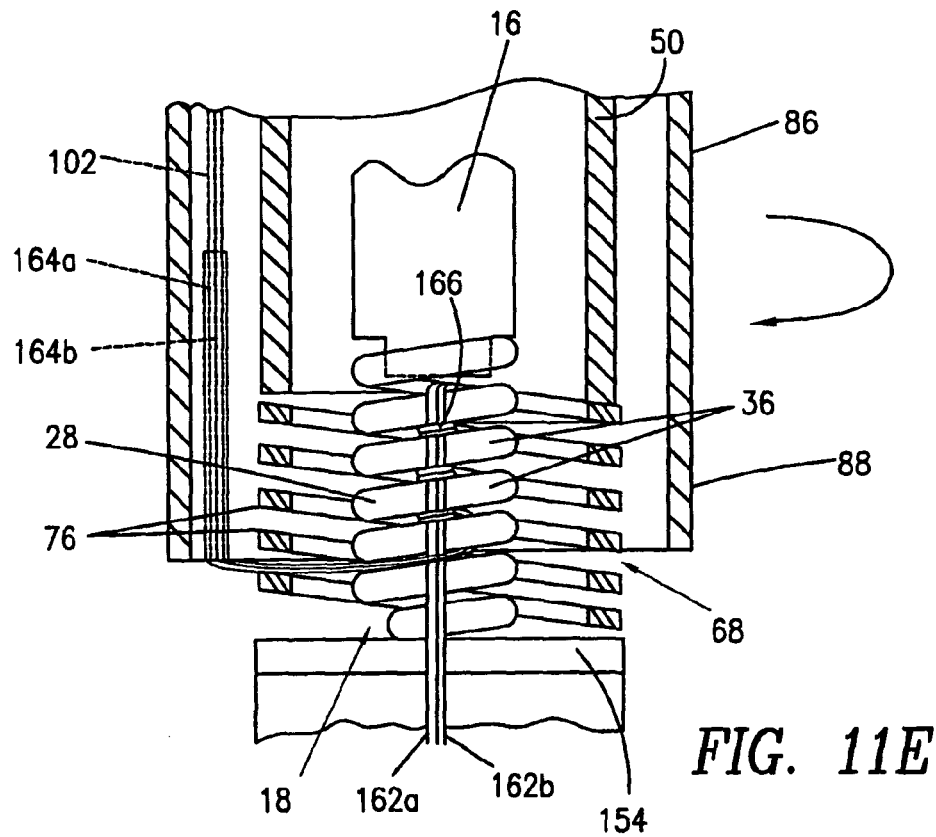

With reference to FIGS. 6 and 11A, each of the helically coiled turns 76 of the helical pilot guide 68 has a pitch which is similar to the pitch of the helically coiled turns 36 of the suture anchoring device 18. In this manner, when the suture anchoring device 18 is properly positioned in the central opening 82 of the helical pilot guide 68 for the performance of the suture anchoring operation, each of the helically coiled turns 76 of the helical pilot guide 68 is substantially or generally aligned with a corresponding one of the helically coiled turns 36 of the suture anchoring device 18. As a result, each of the lateral openings 78 of the helical pilot guide 68 is substantially or generally aligned with a corresponding one of the lateral openings 38 of the suture anchoring device 18. For instance, as shown in FIG. 11A, the two lowermost lateral openings 78a, 78b of the helical pilot guide 68 are generally aligned with the two lowermost lateral openings 38a, 38b of the suture anchoring device 18 in the axial direction. As a result of such alignment, when a suture is wound around the helical pilot guide 68, it is guided into the lateral openings 38 so as to properly secure same to the suture anchoring device 18 as will be discussed in greater detail hereinbelow.

Referring back to FIGS. 1-3, the winding tube assembly 14 includes an outer winding tube 86 projecting from the casing 12. The winding tube 86 includes a distal end 88, which is located opposite the casing 12, and a proximal end 90, which is located in the bore 24 of the casing 12. A bore 92 extends completely through the winding tube 86 between the distal end 88 and the proximal end 90 thereof. The bore 92 is adapted to rotatably receive the pilot guide tube 50 therethrough. The proximal end 90 of the winding tube 86 terminates short of the proximal end 54 of the pilot guide tube 50 (see FIG. 3) such that the gear 58 of the pilot guide tube 50 engages the gear assembly 26 of the casing 12. When the pilot guide tube 50 is rotated by the gear assembly 26 of the casing 12, it moves axially relative to the winding tube 86 between an extended position, in which its helical pilot guide 68 extends axially outwardly from the distal end 88 of the winding tube 86 (see FIGS. 1, 6 and 10C), and a retracted position, in which its helical pilot guide 68 is positioned within the distal end 88 of the winding tube 86 (see FIGS. 2 and 10A). The winding tube 86, which is substantially linear, can be made from any suitable materials (e.g., stainless steel)

A gear 94 (see FIGS. 2, 3, 7B and 8) is fixedly mounted on the winding tube 86 and is positioned in the bore 24 of the casing 12 adjacent the distal end 20 of the winding tube 86. The gear 94 is adapted to engage the gear assembly 26 of the casing 12 so as to rotate the winding tube 86 in a clockwise or counterclockwise direction. The winding tube 86 is also provided with screw threads 96 (see FIGS. 2 and 3) formed adjacent the gear 94 for purposes to be discussed hereinafter.

A bushing 98 (see FIGS. 1-3), which has internal screw threads 100, is mounted to the distal end 20 of the casing 12 for rotatably supporting the winding tube 86. The bushing 98 is affixed to the distal end 20 of the casing 12 by a mounting screw so as to be immovably secured to the casing 12. The winding tube 86 extends through the bushing 98 such that the screw threads 96 of the winding tube 86 constantly engage the screw threads 100 of the bushing 98. In this manner, when the gear 94 of the winding tube 86 is rotated by the gear assembly 26 of the casing 12, the screw threads 96 of the winding tube 86 mate with the screw threads 100 of the bushing 98 so as to cause the winding tube 86 to move axially relative to the casing 12 and the pilot guide tube 50 in a helical path. For instance, by rotating the winding tube 86 in a forward direction (e.g., a counterclockwise direction as indicated by arrow A in FIG. 6A), the winding tube 86 can be moved forward (i.e., away from the proximal end 22 of the casing 12) in the axial direction from its retracted position to its extended position, in which it projects axially outwardly from the distal end 20 of the casing 12 by a predetermined distance. The screw threads 96 of the winding tube 86 and the screw threads 100 of the bushing 98 have a pitch that is similar or substantially identical to the pitch of the helically coiled turns 36 of the suture anchoring device 18 and hence the helically coiled turns 76 of the helical pilot guide 68. As a result, the winding tube 86 is movable axially in a helical path having a pitch similar to the pitch of the helically coiled turns 36 of the suture anchoring device 18 for purposes to be discussed hereinafter.

With reference to FIGS. 6 and 6A, the distal end 88 of the winding tube 86 includes a V-shaped cleft or groove 102 formed therein. The cleft 102 projects into a cylindrical wall of the winding tube 86 in an angled or slanted direction. More particularly, the cleft 102 is slanted or angled in a direction substantially opposite to the forward direction of rotation of the winding tube 86 (i.e., in the direction in which the winding tube 86 rotates when it moves forward from its retracted position to its extended position as indicated by arrow A in FIG. 6A). In this manner, when the winding tube 86 rotates in the forward direction, a suture positioned in the cleft 102 (as indicated by its broken line representation in FIG. 6A) can be retained therein such that it can be wound around the suture anchoring device 18 as will be discussed in greater detail hereinafter.

Referring to FIGS. 1, 7 and 8, the casing 12 is sized and shaped so as to be held by one or both hands of a surgeon. The casing 12 has a pair of casing sections 12a, 12b removably attached to one another. The casing 12 also has a pair of vertically oriented tracks 104, 106 formed therein. Actuators 108, 110, which are movably mounted to the casing 12, have knobs 112, 114, respectively, each of which is positioned outside of the casing 12 and adapted to be pushed by a surgeon's finger. The actuators 108, 110 are also provided with racks 116, 118, respectively, each of which has a plurality of gear teeth 120. The racks 116, 118 are mounted in the tracks 104, 106, respectively, of the casing 12 such that they are movable in a vertical direction. Rods 122, 124 connect the racks 116, 118, respectively, to the knobs 112, 114, respectively, such that the racks 116, 118 are vertically movable in response to the actuation of the knobs 112, 114, respectively.

With reference to FIGS. 7, 7A, 7B and 8, the gear assembly 26 of the casing 12 is provided with a plurality of gears 126, 128, 130, 132 and a plurality of gears 134, 136, 138, 140 rotatably mounted in the casing 12 for rotating the gear 58 of the pilot guide tube 50 and the gear 94 of the winding tube 86, respectively. The gears 126, 128, 134, 136 are arranged substantially linearly in the casing 12 in the axial direction, while the gears 130, 132, 138, 140 are also arranged substantially linearly in the casing 12 in the axial direction. The gear 126 is in constant engagement with the rack 118 such that it can be rotated in response to the vertical movement of the rack 118. The gear 126 is coupled to the gear 128 such that the gear 128 is rotatable conjointly with the gear 126. The gear 130, which is positioned below the gear 128, is in engagement with the gear 128, while the gear 132 is coupled to the gear 130 such that it is conjointly rotatable with the gear 130 in response to the rotation of the gear 128. The gear 58 of the pilot guide tube 50 is positioned laterally from the gear 132 and is in engagement therewith such that the gear 58 and hence the pilot guide tube 50 are rotatable in response to the rotation of the gear 132. In this manner, the gear 58 of the pilot guide tube 50 can be selectively rotated by moving the knob 114 in the vertical direction, thereby moving the pilot guide tube 50 in the axial direction relative to the housing 12 and the winding tube 86.

Referring to FIGS. 7, 7B and 8, the gear 134 is in constant engagement with the rack 116 such that it can be rotated in response to the vertical movement of the rack 116. The gear 136 is coupled to the gear 134 such that it is rotatable conjointly with the gear 134. The gear 138, which is positioned below the gear 136, is in constant engagement with the gear 136, while the gear 140 is coupled to the gear 138 such that it is rotatable conjointly with the gear 138. The gear 94 of the winding tube 86 is positioned laterally from the gear 140 and is in engagement therewith such that the gear 94 and hence the winding tube 86 are rotatable in response to the rotation of gear 140. In this manner, by moving the knob 112 and hence the rack 116 in the vertical direction, the gear 94 can be selectively rotated so as to cause the winding tube 86 to be rotated and moved in the axial direction relative to the casing 12 and the pilot guide tube 50.

While the gear 134 and the gear 126 have a common mounting rod 142a (see FIGS. 7 and 8) therebetween, they rotate independently from one another (i.e., they are not conjointly rotatable). Likewise, although the gear 130 and the gear 138 have a common mounting rod 142b (see FIG. 7) therebetween, they rotate independently from one another. As a result, the vertical movement of the rack 118 does not cause the gear 134 to rotate, and the vertical movement of the rack 116 does not cause the gear 126 to rotate. In such circumstances, the actuator 108 controls the axial movement of the winding tube 86, while the actuator 110 controls the axial movement of the pilot guide tube 50.

Figure 12A:
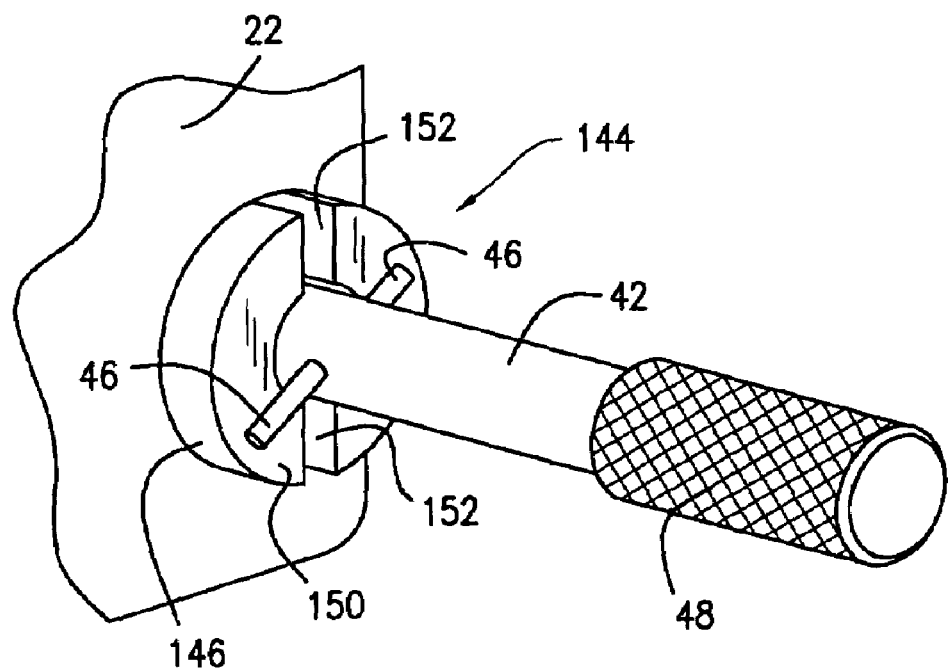
FIG. 12A is a perspective view of a portion of a proximal end of the suture winding device shown in FIG. 1, illustrating a fitting of the casing and a proximal end of the support rod.
Figure 12B:
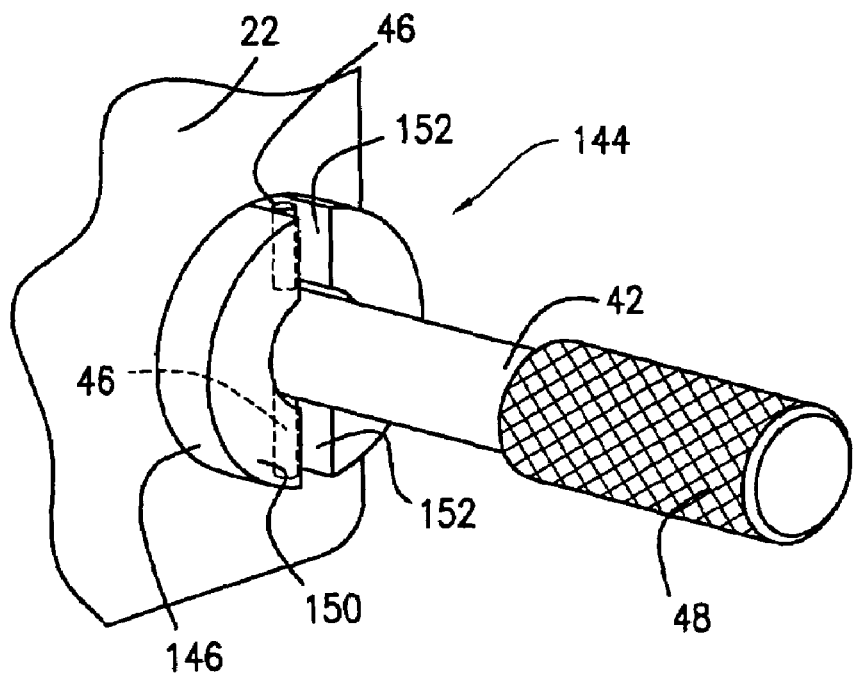
FIG. 12B is a view similar to FIG. 12A, except that the support rod is inserted fully into the casing of the suture winding device.

Now referring to FIGS. 3, 12A and 12B, the casing 12 is also equipped with a fitting 144 positioned at the proximal end 22 thereof. More particularly, the fitting 144 includes a flange 146 abutting the proximal end 22 of the casing 12. A cylindrical section 148 (see FIG. 3) projects from the flange 146 and is positioned in the bore 24 of the casing 12 for receiving the support rod 16 therethrough. The flange 146 includes an outer surface 150 and a pair of slots 152. The slots 152 are formed in the flange 146 and are sized and shaped so as to receive the pins 46 of the support rod 16. The slots 152 permit the support rod 16 to be positioned in two different axial positions (see FIGS. 12A and 12B) as will be discussed in greater detail hereinafter.

The operation of the suture winding device 10 will be discussed hereinafter in conjunction with a suture used for attaching a valve ring to an artery of a heart. It should be understood, however, that the following description is only meant to be illustrative of the present invention and is not meant to limit the scope of the present invention, which has applicability to sutures used in other types of medical procedure or surgery.

Figure 9A:
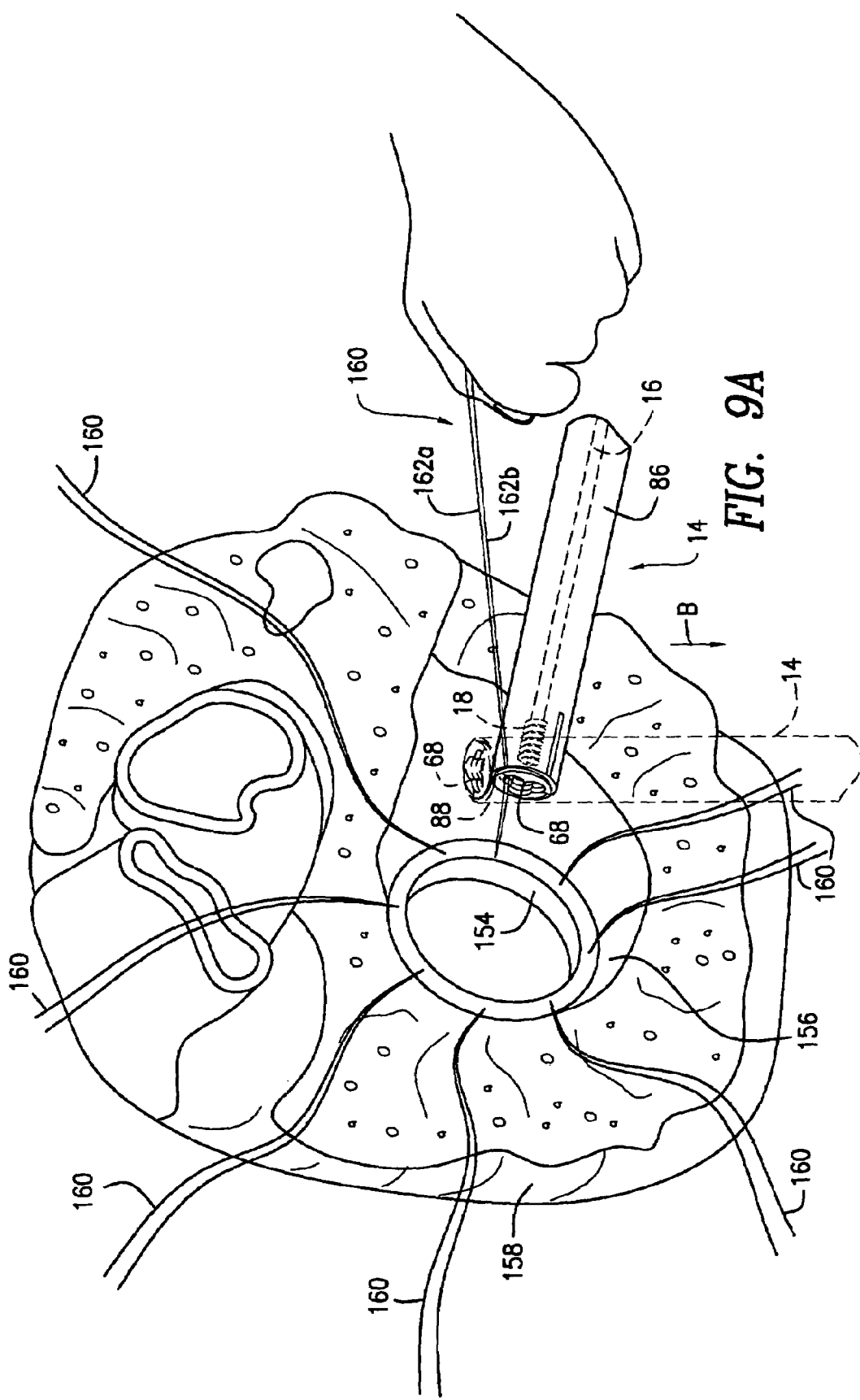
FIGS. 9A-9C are schematic views of the suture winding device shown in FIG. 1 during the deployment of the suture anchoring device to a valve ring sutured to a heart.

With reference to FIG. 9A, a valve ring 154 is initially attached to an artery 156 of a heart 158 with the use of sutures 160 in a conventional manner. Prior to the deployment of a suture anchoring device 18 to each of the sutures 160, the winding tube 86 and the pilot guide tube 50 are positioned in their retracted positions (i.e., initial deployment positions as shown in FIGS. 2 and 10A). More particularly, the winding tube 86 is retracted into the casing 12 (i.e., the knob 112 is in its upper position as indicated by the solid line representation of the knob 112 in FIG. 7). Likewise, the pilot guide tube 50 is retracted into the winding tube 86 such that the entire helical pilot guide 68 of the pilot guide tube 50, with the exception of its lowermost helically coiled turn or tip 76a (see FIG. 10A), is positioned within the distal end 88 of the winding tube 86 (i.e., the knob 114 is in its upper position as indicated by the solid line representation of the knob 114 in FIG. 7). That is, in its initial deployment position, the pilot guide tube 50 has its lowermost helically coiled turn or tip 76a projecting axially outwardly from the distal end 88 of the winding tube 86 (see FIG. 10A).

The support rod 16, together with the suture anchoring device 18 removably mounted thereto, is also inserted into the bore 24 of casing 12 until the pins 46 abut the outer surface 150 of the fitting 144 of the casing 12 (see FIG. 12A), preventing further advancement of the support rod 16 toward the distal end 88 of the winding tube 86 and thereby positioning the support rod 16 and hence the suture anchoring device 18 in their initial deployment positions (see FIG. 10A). More particularly, when the support rod 16 is placed in this initial deployment position, the entire portion of the suture anchoring device 18 is positioned within the distal end 88 of the winding tube 86.

Strands 162a, 162b of a selected one of the sutures 160 are pulled by the surgeon away from the surgical site (i.e., the valve ring 154) so as to provide sufficient tension therein. With the winding tube 86, the pilot guide tube 50 and the support rod 16 positioned in their initial deployment positions, the winding tube assembly 14 is positioned such that it is oriented substantially perpendicular relative to the suture strands 162a, 162b (see the broken line representation of the winding tube assembly 14 in FIG. 9A). While being urged against the suture strands 162a, 162b, the winding tube assembly 14 is moved away from the suture strands 162a, 162b (as indicated by arrow B in FIG. 9A) in a substantially perpendicular direction (i.e., in a direction substantially perpendicular to the suture strands 162a, 162b). When the suture strands 162a, 162b reach the distal end 88 of the winding tube 86, they fall into the lateral opening 78a formed between the lowermost helically coiled turn 76a and its adjacent helically coiled turn 76b of the helical pilot guide 68 (see FIGS. 9A and 10A). The winding tube assembly 14 is then rotated such that the suture strands 162a, 162b and the winding tube assembly 14 are pointed toward the surgical site (see the solid line representation of the winding tube assembly 14 in FIG. 9A).

After positioning the suture strands 162a, 162b in the lateral opening 78a of the helical pilot guide 68 and orienting the winding tube assembly 14 toward the surgical site, the knob 114 of the casing 12 is depressed by the surgeon such that the rack 118 is moved downwardly from its upper position to its lower position, causing the gear 126 (see FIGS. 7 and 8) to rotate. In response, the gear 126 causes the gears 128, 130, 132 (see FIGS. 7 and 8) to rotate, thereby rotating the gear 58 of the pilot guide tube 50. As a result, the pilot guide tube 50 is rotated and is hence advanced forward in the axial direction toward its extended position. The support rod 16 and the winding tube 86 remain stationary during the forward axial movement of the pilot guide tube 50 to its extended position. As a result, the suture anchoring device 18 mounted to the support rod 16 remains within the distal end 88 of the winding tube 86 (see FIG. 10B).

Figure 9B:
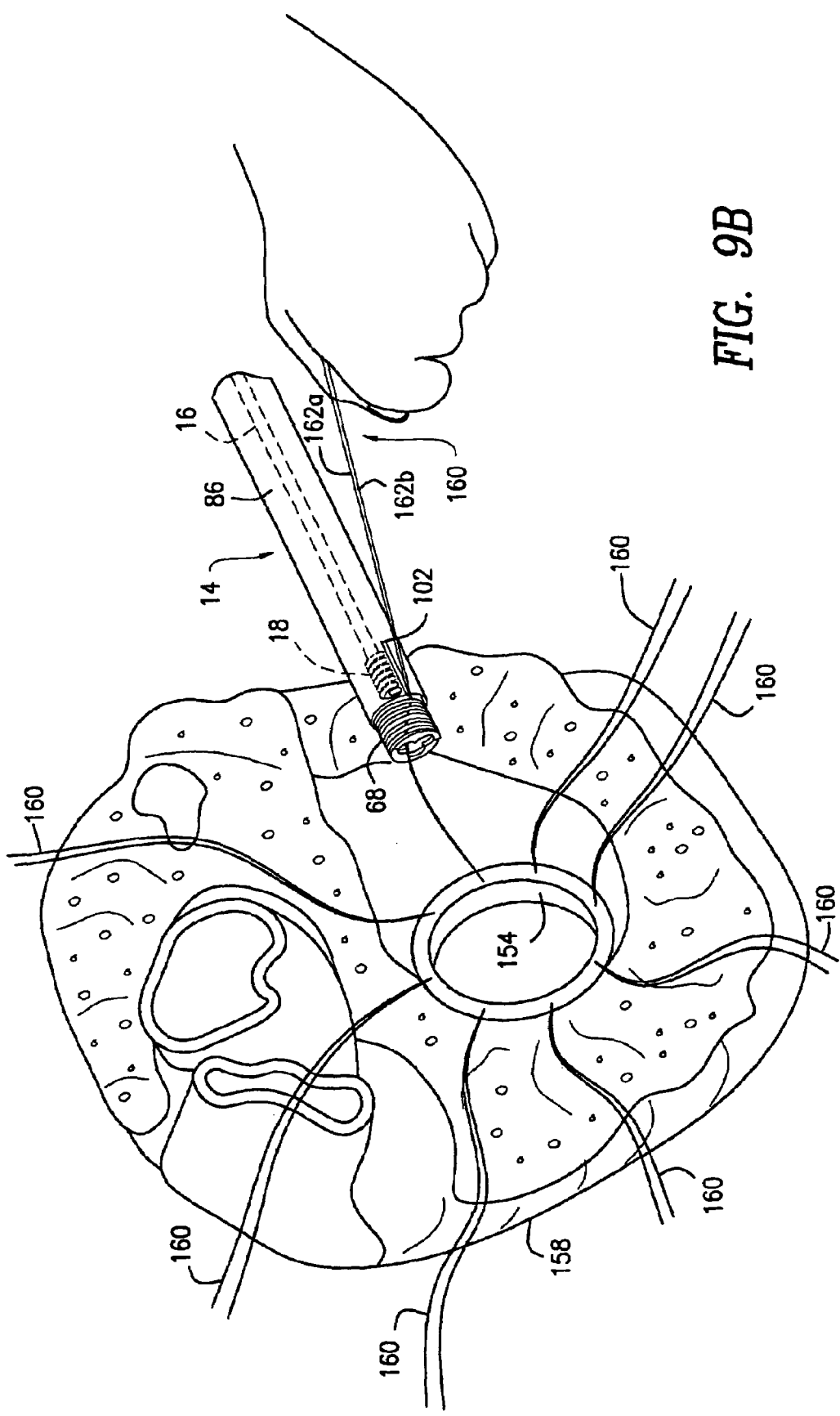
Figure 9C:
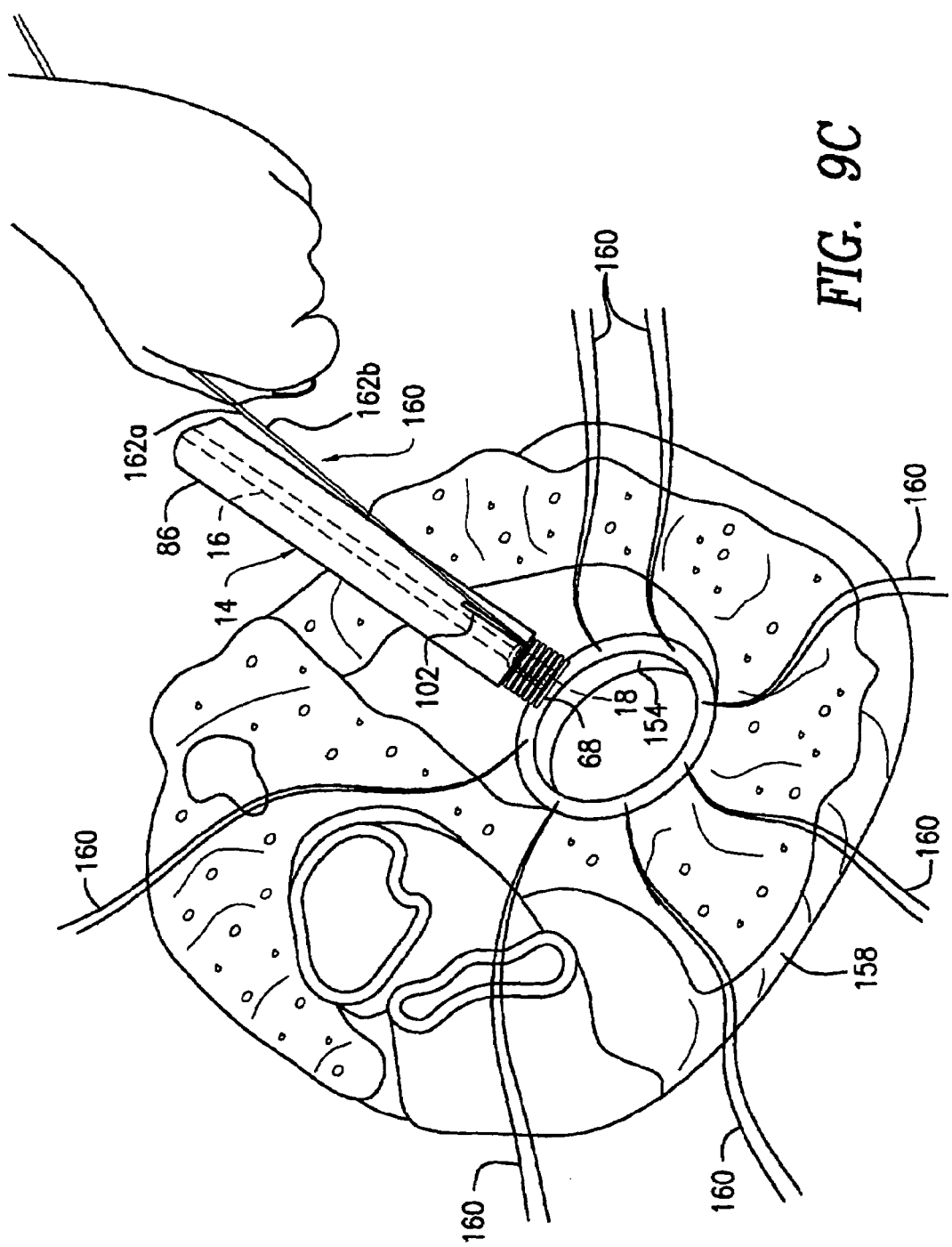

As the pilot guide tube 50 and hence the helical pilot guide 68 advance forward in helical fashion, the suture strands 162a, 162b are passed upward through the lateral openings 78 of the helical pilot guide 68 (see FIG. 10B). In this manner, when the pilot guide tube 50 is advanced to its fully extended position, the suture strands 162a, 162b are positioned in the central opening 82 of the helical pilot guide 68 (see FIGS. 9B and 10C). That is, the suture strands 162a, 162b extend into the central opening 82 through the distal end 72 of the helical pilot guide 68 and exit same through the lateral opening 78c formed between the two uppermost helically coiled turns 76c, 76d of the helical pilot guide 68 (see FIG. 10C).

After moving the pilot guide tube 50 to its extended position and thereby positioning the suture strands 162a, 162b through the helical pilot guide 68, the gripping area 48 (see FIGS. 12A and 12B) of the support rod 16 is rotated by the surgeon such that the pins 46 are aligned with the slots 152 of the fitting 144 of the casing 12, thereby permitting further advancement of the support rod 16 into the casing 12. More particularly, each of the slots 152 is sized and shaped so as to receive a corresponding one of the pins 46 (see FIG. 12B) and is provided with a predetermined depth such that the support rod 16 can be advanced forward by a preset distance. As a result, the suture anchoring device 18 is advanced by the same preset distance so as to be positioned in the central opening 82 of the helical pilot guide 68 (see FIG. 10D).

Referring now to FIG. 6A, when the suture anchoring device 18 is properly positioned in the central opening 82 of the helical pilot guide 68, it is radially surrounded, and hence supported, by the lobes 80 of the helical pilot guide 68. The suture strands 162a, 162b are also positioned in one of the circular spaces 84 formed by the lobes 80 such that they extend between the outer sides of the helically coiled turns 28 of the suture anchoring device 18 and the interior sides of the helically coiled turns 76 of the helical pilot guide 68 (see FIGS. 6A and 10D). In addition, as discussed above, the pitch of the helical configuration of the helical pilot guide 68 is similar to the pitch of the helical configuration of the suture anchoring device 18. As a result, the lateral opening 78 formed between each adjacent pair of the helically coiled turns 76 of the helical pilot guide 68 is substantially aligned in the axial direction with a corresponding one of the lateral openings 38 formed by the helically coiled turns 36 of the suture anchoring device 18 (see FIG. 11A). In other words, each of the helically coiled turns 76 of the helical pilot guide 68 is substantially aligned with a corresponding one of the helically coiled turns 36 of the suture anchoring device 18 in the axial direction. The helical pilot guide 68 and the suture anchoring device 18 are preferably constructed such that the foregoing conditions automatically exist when the support rod 16 is inserted fully into the casing 12.

Figure 10E:
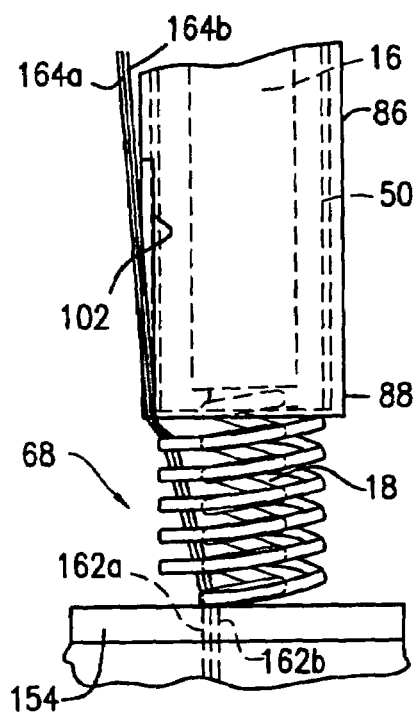

After positioning the support rod 16 into its fully inserted position, the suture winding device 10 is moved toward the surgical site (i.e., the valve ring 154) such that the helical pilot guide 68 and the suture anchoring device 18 are pressed against the surgical site (see FIG. 10E). Next, external segments 164a, 164b of the suture strands 162a, 162b, respectively, (i.e., the segments of the suture strands 162a, 162b extending outwardly from the helical pilot guide 68) are positioned in the cleft 102 of the winding tube 86 and then are pulled by the surgeon away from the surgical site such that sufficient tension is provided in the suture 160. The knob 112 of the casing 12 is then depressed by the surgeon so as to move same from its upper position (indicated by the solid line representation of the knob 112 in FIG. 7) to its lower position (indicated by the broken line representation of the knob 112 in FIG. 7) such that the rack 116 is moved downwardly, causing the gear 134 (see FIGS. 7 and 8) to rotate. In response, the gears 136, 138, 140 (see FIGS. 7 and 8) rotate so as to cause the gear 94 and hence the winding tube 86 to rotate in a direction that is identical to the direction of rotation of the pilot guide tube 50 during its movement from the retracted position to the extended position. As a result, the winding tube 86 is advanced from its retraced position toward its extended position. Because the cleft 102 is angled in a direction substantially opposite to the direction of rotation of the winding tube 86 (see FIG. 6A), the external suture segments 164a, 164b are retained in the cleft 102 (as indicated by the broken line representation of the external suture segments 164a, 164b in FIG. 6A) and are thereby wound around the suture anchoring device 18 for lashing the suture strands 162a, 162b to each helically coiled turn 36 of the suture anchoring device 18.

The process utilized by the suture winding device 10 for lashing the suture strands 162a, 162b to the suture anchoring device 18 will be discussed in greater detail hereinafter. To facilitate consideration and discussion, it is noted that the lashing process utilized by the suture winding device 10 is similar or basically identical to the lashing process disclosed in co-pending, commonly owned U.S. patent application Ser. No. 10/122,970, except that the lashing process of the present invention is performed with the use of the suture winding device 10.

Figure 11F:
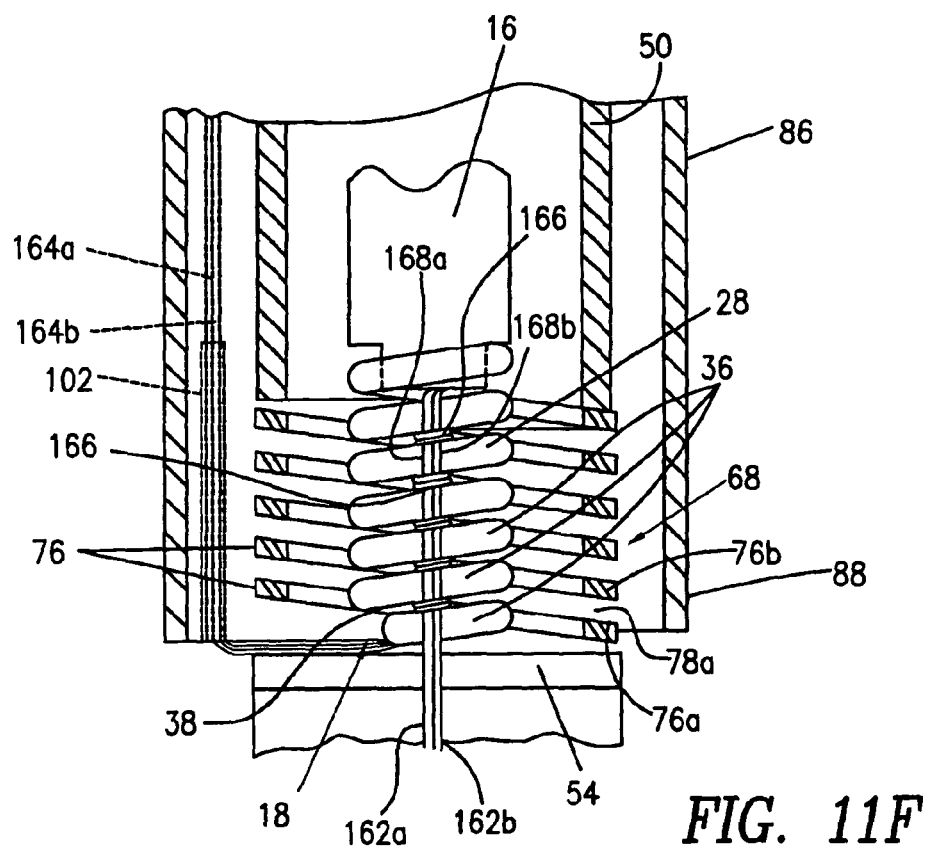

With reference to FIGS. 11A-11F, as the winding tube 86 rotates, the external suture segments 164a, 164b are caused to wind down along the helically coiled turns 76 of the helical pilot guide 68, beginning with the helically coiled turn 76c located immediately below the uppermost helically coiled turn 76d (i.e., the lower one of the pair of the helically coiled turns 76 interposing the suture strands 162a, 162b). As the external suture segments 164a, 164b travel back down along the initial helical turn 76c of the helical pilot guide 68, they pass through the lateral opening 78c formed between the helically coiled turns 76c, 76d and are guided into the lateral opening 38c formed between a corresponding pair of the helically coiled turns 36 of the suture anchoring device 18 (i.e., the helically coiled turns 36a, 36b in FIGS. 11A and 11B). As a result, when the winding tube 86 makes a first complete revolution (see FIGS. 11A-11C), the external suture segments 164a, 164b are looped over the helically coiled turn 36a of the suture anchoring device 18. Thereafter, as the winding tube 86 makes additional revolutions, the external suture segments 164a, 164b are wound through each of the subsequent helically coiled turns 36 of the suture anchoring device 18 such that the external suture segments 164a, 164b are wound back down the coiled member 28 along the helical path of the suture anchoring device 18 in order to lash the suture strands 162a, 162b to the suture anchoring device 18 (see FIGS. 11C-11F). As shown in FIG. 11F, the suture strands 162a, 162b are wrapped about each of the helically coiled turns 36 of the coiled member 28 such that the suture strands 162a, 162b are frapped about themselves in order to create a multiple frapping arrangement 166. This frapping process results when the suture strands 162a, 162b are forced downward by each helically coiled turn 36 where the suture strands 162a, 162b catch upon their internal segments 168a, 168b (i.e., the segments of the suture strands 162a, 162b that extend between the helically coiled turns 36 of the suture anchoring device 18 and the helically coiled turns 76 of the helical pilot guide 68) such that one frapping arrangement 34 occurs per revolution of the suture strands 162a, 162b. The lashing of the suture strands 162a, 162b to each of the helically coiled turns 36 of the coiled member 28 negates the movement of the suture strands 162a, 162b. The frapping arrangement 166 (of the suture strands 162a, 162b) helps maximize the internal frictional forces by removing slack from the suture strands 162a, 162b, as depicted in FIG. 11F.

As used herein, the term "lashing" is defined as a binding with a suture used for fastening. A lashing is typically comprised of a combination of wrappings and frappings. A "wrapping", as used herein, is defined as a portion of a lashing which secures a section of suture(s) that is directly against and in contact with the suture anchoring device 18. A "frapping", as used herein, is defined as a portion of a lashing which serves to remove slack from the lashing. This is accomplished by pulling one section of the suture(s) over other portions of the suture(s) that are in contact with each other.

As discussed above, when the suture anchoring device 18 is properly positioned in the helical pilot guide 68, each of the helically coiled turns 36 of the suture anchoring device 18 is substantially or generally aligned with a corresponding one of the helically coiled turns 76 of the helical pilot guide 68. As a result, during the lashing operation, the helically coiled turns 76 of the helical pilot guide 68 and their lobes 80 function to properly guide the external suture segments 164a, 164b into the lateral openings 38 formed between the helically coiled turns 36 of the suture anchoring device 18. In other words, because of the helically coiled turns 76 of the helical pilot guide 68, portions of the external suture segments 164a, 164b to be inserted into a corresponding one of the lateral openings 38 of the suture anchoring device 18 (e.g., portions 169 of the suture strands 162a, 162b in FIG. 11B) are substantially coplanar with the corresponding lateral opening 38 (e.g., the lateral opening 38c in FIG. 11B), thereby facilitating the lashing of the suture strands 162a, 162b to the suture anchoring device 18.

As discussed above, the winding tube 86 advances forward from its retracted position to its extended position in a helical path having a pitch which is similar or substantially identical to the pitch of the helical configuration of the suture anchoring device 18 and hence the helical configuration of the helical pilot guide 68 of the pilot guide tube 50. In this manner, the distal end 88 of the winding tube 86 advances forward following the path of the helical coiled rod 28 of the suture anchoring device 18 and therefore the path of the helical coiled rod 70 of the helical pilot guide 68, thereby facilitating the insertion of the suture strands 162a, 162b into the suture anchoring device 18 while permitting same to pass through the helical pilot guide 68.

During the lashing operation, the internal suture segments 168a, 168b (i.e., the segments of the suture strands 162a, 162b positioned between the helically coiled turns 76 of the helical pilot guide 68 and the helically coiled turns 36 of the suture anchoring device 18) are retained in the circular space 84 formed between a corresponding pair of the lobes 80 (see the broken line representation of the internal suture segments 168a, 168b in FIG. 6A). More particularly, the tips 80a of the lobes 80 terminate immediately adjacent to the suture anchoring device 18 such that gaps formed between the tips 80a of the lobes 80 and the suture anchoring device 18 are smaller than the diameter of the suture 160, thereby inhibiting the internal suture segments 168a, 168b from moving out of the corresponding circular space 84. As a result, the frapping arrangement 166 occurs in the corresponding circular space 84. Each of the circular spaces 84 is sized and shaped such that sufficient clearance is formed between the helical pilot guide 68 and the frapping arrangement 166 formed on the suture anchoring device 18. In this manner, after the completion of the lashing operation, the suture winding device 10 can be separated easily from the suture anchoring device 18.

Figure 10F:
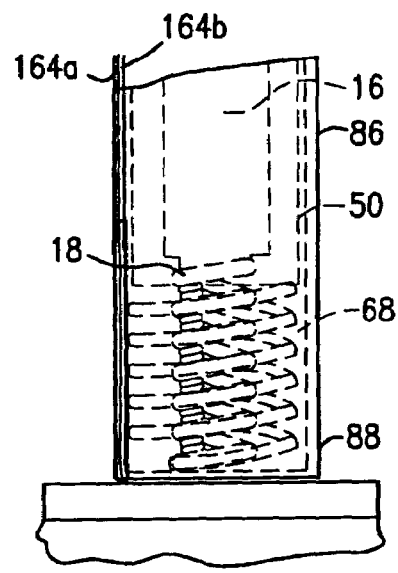
Figure 10G:
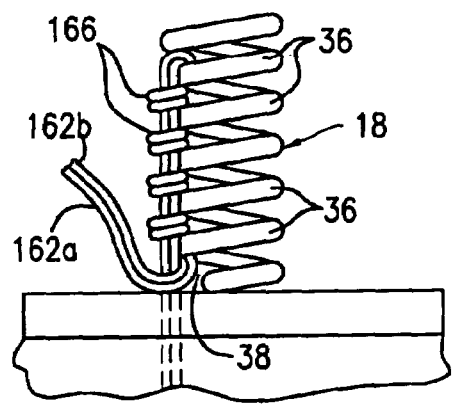

When the winding tube 86 is moved to its extended position as shown in FIGS. 10F and 11F, the external suture segments 164a, 164b are decoupled from the helical pilot guide 68 through the lateral opening 78a formed between the lowermost helically coiled turn 76a and its adjacent helically coiled turn 76b (see FIG. 11F). The suture winding device 10 is then removed from the surgical site, leaving the suture anchoring device 18 secured to the suture strands 162a, 162b (see FIG. 10G). More particularly, the retracting movement of the suture winding device 10 causes the suture anchoring device 18 to be detached from the support rod 16 and hence the suture winding device 10. The suture strands 162a, 162b are then cut, leaving only small tails at the distal end 40 of the suture anchoring device 18.

In order to perform another suture anchoring operation, the knobs 112, 114 are moved back to their upper positions, thereby causing the winding tube 86 and the pilot guide tube 50 to retract to their retracted positions. The support rod 16 is also removed from the suture winding device 10. A new suture anchoring device is then loaded onto the mounting tip 44 of the support rod 16. Next, the support rod 16 is re-inserted into the suture winding device 10 together with the new suture anchoring device. Alternatively, the support rod 16 can be removed from the suture winding device 10 and be replaced with an identical support rod which has a suture anchoring device mounted thereon. In this manner, the loading of a new suture anchoring device into the suture winding device 10 can be facilitated. By preparing in advance multiple support rods with suture anchoring devices, the suture winding device 10 can be used for performing multiple suture anchoring operations in an accelerated manner.

It should be appreciated that the present invention provides a device for securing a suture to the suture anchoring device 18 in a substantially automatic manner. As a result, by using the suture winding device 10, the suture anchoring device 18 can be easily and efficiently deployed at a surgical site. For instance, the suture winding device 10 can be used to lash a suture to a suture anchoring device in a confined or non-confined work area or remote surgical site (e.g., wound sites in endoscopic, laparoscopic or arthroscopic procedures).

It should be noted that the suture winding device 10 can have numerous modifications and variations. For instance, the helical pilot guide 68 of the pilot guide tube 50 can be provided with a different construction for supporting the suture anchoring device 18 therein, guiding a suture or sutures into the suture anchoring device 18 and/or retaining the interior suture segments during the performance of the lashing operation. By way of example, the lobes 80 can be eliminated, and the helical pilot guide 68 can be provided with other geometrical or non-geometrical shape, such as a tear-drop or oval shape, suitable for performing one or more of these functions. The cleft 102 of the winding tube 86 can also be eliminated or replaced with other mechanisms (e.g., a hook extending from the distal end 88 of the winding tube 86 and sized and shaped so as to engage one or more sutures). In addition, the mounting tip 44 of the support rod 16 can be threaded so as to promote enhanced engagement between the suture anchoring device 18 and the support rod 16. The suture winding device 10 can also be modified for use in non-medical procedures to secure a rope, a string filament or the like to any coiled rod having a helical configuration.

It should be noted that the suture winding device 10 can be used in conjunction with the suture anchoring device 18 having a construction different from the construction illustrated in FIG. 5. For instance, the suture anchoring device 18 can be constructed such that each of the lateral openings 38 formed in the suture anchoring device 18 is provided with a dimension (i.e., a distance between each adjacent pair of the helically coiled turns 36) that is smaller than the thickness or diameter of a suture. As a result, the dimension of each of the lateral openings 38 can be smaller than the dimension of a corresponding one of the lateral openings 78 of the helical pilot guide 68 of the pilot guide tube 50. Alternatively, the coiled helical rod 28 of the suture anchoring device 18 can be wound such that no lateral opening 38 is formed between each adjacent pair of the helically coiled turns 36 (i.e., each of the helically coiled turns 36 is in contact with its adjacent pair). When the suture anchoring device 18 is provided with one of the foregoing constructions, the coiled helical rod 28 is made elastic such that it is axially expandable from its collapsed state to its expanded state, in which the lateral openings 38 are formed or have a greater dimension. When the suture anchoring device 18 is positioned in the helical pilot guide 68, the lateral openings 38 (with the exception of the uppermost lateral opening 38c which initially receives a suture at the beginning of a lashing operation) do not align with their corresponding lateral openings 78 of the helical pilot guide 68. As the suture is wound around the suture anchoring device 18 and is thereby inserted into adjacent pairs of the helically coiled turns 36 of the suture anchoring device 18, the coiled helical rod 28 expands axially from its collapsed state to its expanded state such that each subsequent lateral opening 38 of the suture anchoring device 18 aligns sequentially with a corresponding one of the lateral openings 78 of the helical pilot guide 68, thereby permitting the lashing of the suture to the helically coiled turns 36.

The suture winding device 10 can also be provided with various mechanisms for performing additional functions. For instance, the suture winding device 10 can be equipped with a cutting mechanism (e.g., a blade) incorporated directly in or on the winding tube 86 for cutting a suture after the performance of a suture anchoring operation. The suture winding device 10 can also be equipped with a tensioning mechanism for maintaining proper tension in the suture strands 162a, 162b during the performance of the lashing operation. Such a mechanism can be in the form of a high friction grommet having an oblong shape. Alternatively, a spring-loaded member having a tensioning feature can be mounted directly on the winding tube 86. During the performance of the lashing operation, a suture can be secured to the spring-loaded member, which is movable in a direction substantially parallel to the longitudinal axis of the winding tube 86 when the tension force in the suture is different from the force applied by the spring. Graduated markings can also be provided on the winding tube 86 to indicate the amount of tension present in the suture.

FIGS. 13-18 depict a second embodiment of the present invention. Elements illustrated in FIGS. 13-18, which correspond, either identically or substantially, to the elements described above with respect to the embodiment illustrated in FIGS. 1-12, have been designated by corresponding reference numerals increased by one thousand. Unless otherwise stated, the embodiment of FIGS. 13-18 is basically identical, in construction and operation, to the embodiment of FIGS. 1-12.

Figure 13:
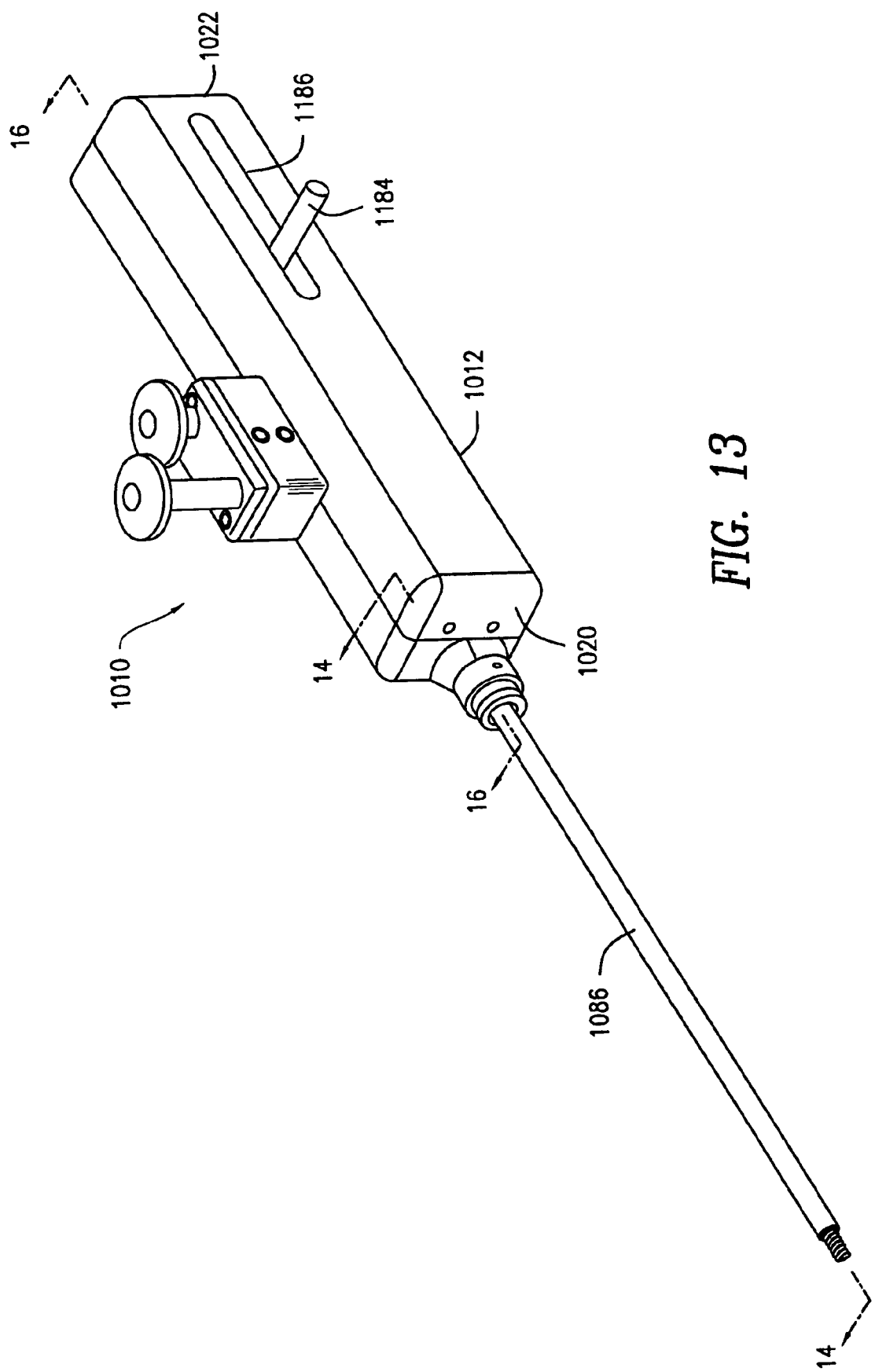
FIG. 13 is a perspective view of a suture winding device constructed in accordance with a second embodiment of the present invention.

With reference to FIG. 13, there is shown a suture winding device 1010 constructed in accordance with the second embodiment of the present invention. The suture winding device 1010 includes a casing 1012 having a proximal end 1022, a distal end 1020 and a bore 1024 extending therethrough between the proximal end 1022 and the distal end 1020. The suture winding device 1010 is also equipped with an outer winding tube 1086 and a pilot guide tube 1050 projecting from the distal end 1020 of the casing 1012. The pilot guide tube 1050 extends through the winding tube 1086 and includes a bore 1056, which extends through therethrough, and a helical pilot guide 1068, which is located at a distal end 1052 thereof. The suture winding device 1010 also has a support rod 1016 extending through the bore 1024 of the casing 1012 and the bore 1056 of the pilot guide tube 1050. The suture winding device 1010 is identical, in construction and operation, to the suture winding device 10 of the embodiment illustrated in FIGS. 1-12B, except that the suture winding device 1010 is equipped with a multifeed mechanism for feeding multiple suture anchoring devices loaded into the suture winding device 1010 without removing or replacing the support rod 1016 after the performance of each suture anchoring operation. The multifeed mechanism of the suture winding device 1010 will be discussed in detail hereinbelow.

Figures 14, 15:
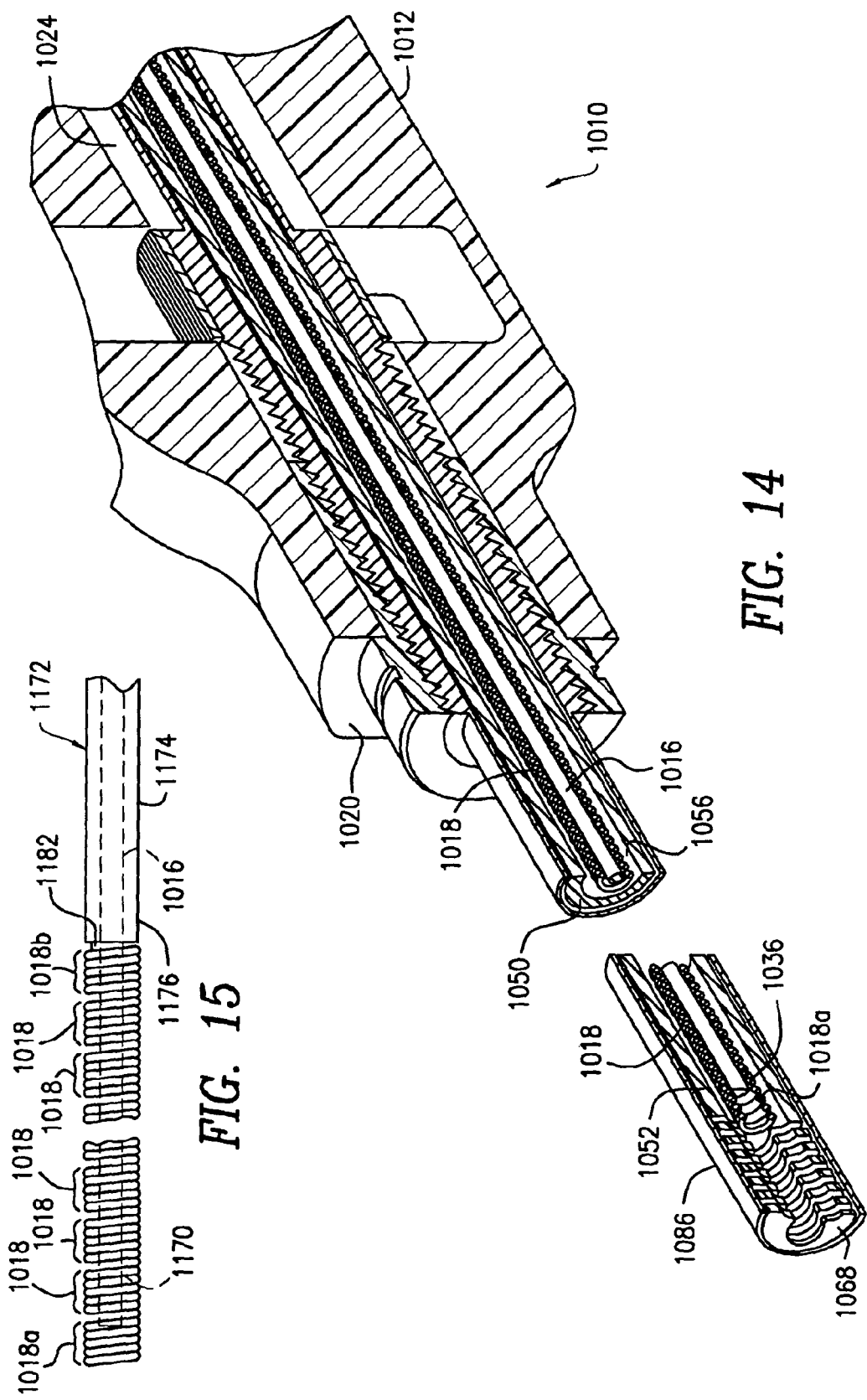
FIG. 14 is a cross-sectional view, taken along section line 14-14 and looking in the direction of the arrows, of the suture winding device shown in FIG. 13.
FIG. 15 is a side elevational view of a support rod of the suture winding device shown in FIG. 13, an array of suture anchoring devices being loaded on the support rod.
Figure 16:
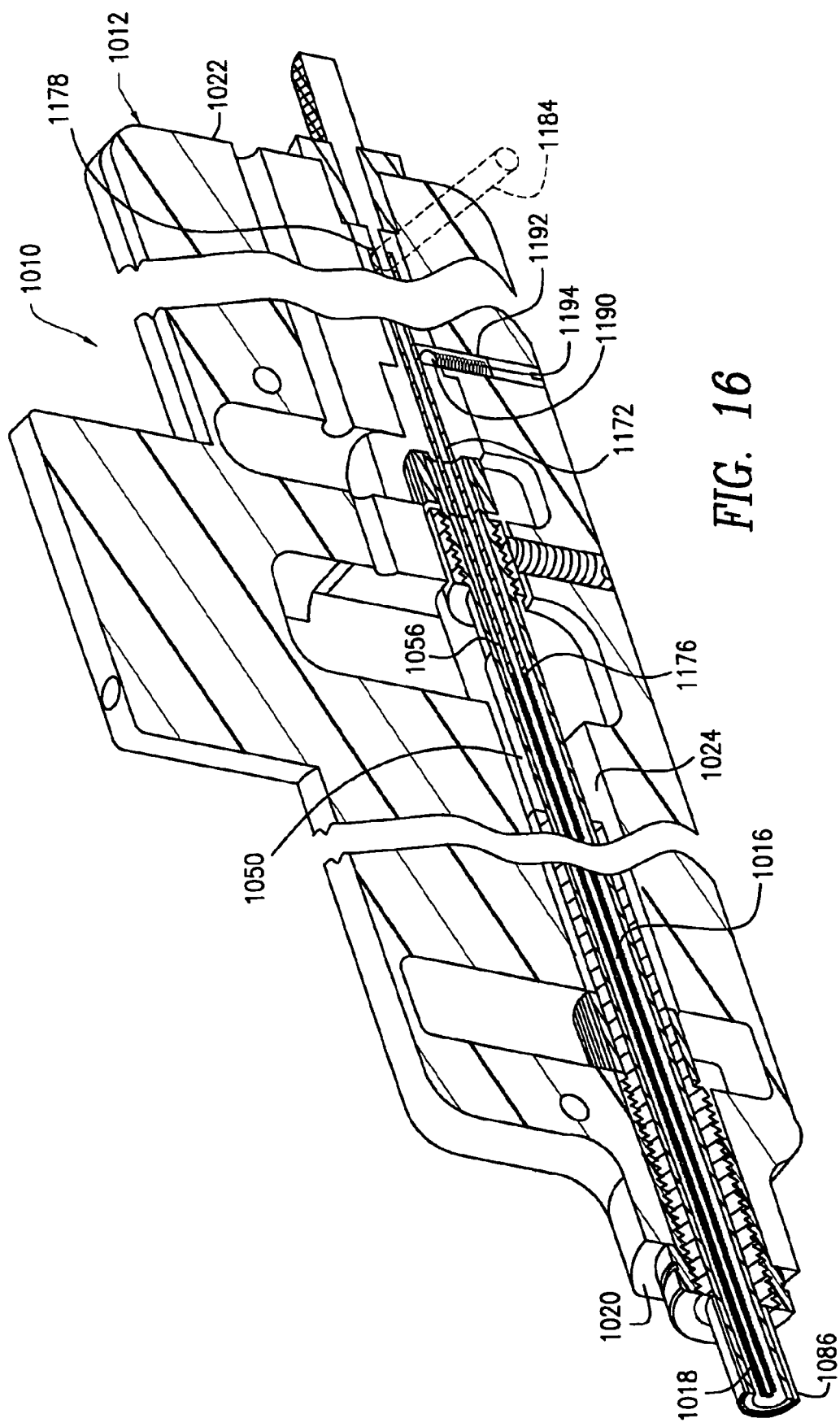
FIG. 16 is a cross-sectional view, taken along section line 16-16 and looking in the direction of the arrows, of the suture winding device shown in FIG. 13.

With reference to FIGS. 14-16, the support rod 1016 has a substantially cylindrical, rigid body 1170 extending between distal and proximal ends 1040, 1042 thereof. The rigid body 1170 is sized and shaped such that an array of multiple suture anchoring devices 1018 (e.g., an array including about twenty (20) suture anchoring devices) can be loaded thereonto. More particularly, the rigid body 1170 of the support rod 1016 extends through central openings formed in the suture anchoring devices 1018 such that the suture anchoring devices 1018 are arranged substantially linearly in an axial direction (i.e., in a direction substantially parallel to the longitudinal axis of the suture winding device 1010). The suture anchoring devices 1018 are also movably mounted on the rigid body 1170 of the support rod 1016 such that they can be advanced axially forward subsequent to the performance of each suture anchoring operation. The distal end 1040 of the support rod 1016 is sized and shaped so at to engage at least one helically coiled turn 1036 of the suture anchoring device 1018a positioned at the forward (i.e., distal) end of the array of the suture anchoring devices 1018 such that it can be properly supported and positioned in the helical pilot guide 1068 by the support rod 1016 for the winding of a suture around the suture anchoring device 1018a.

Figure 17:
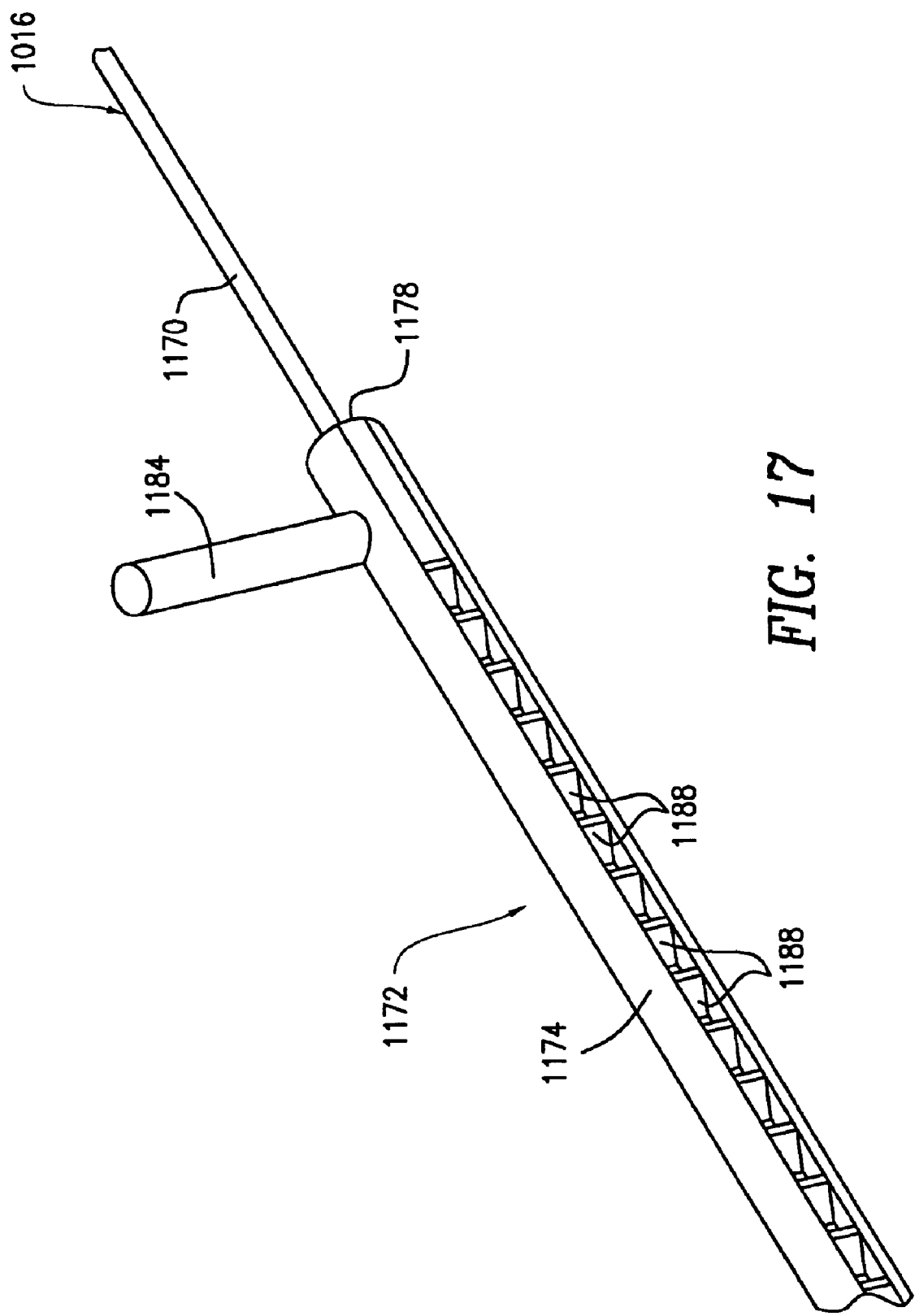
FIG. 17 is a perspective view of a multi-feed mechanism utilized in the suture winding device shown in FIG. 13.
Figure 18:
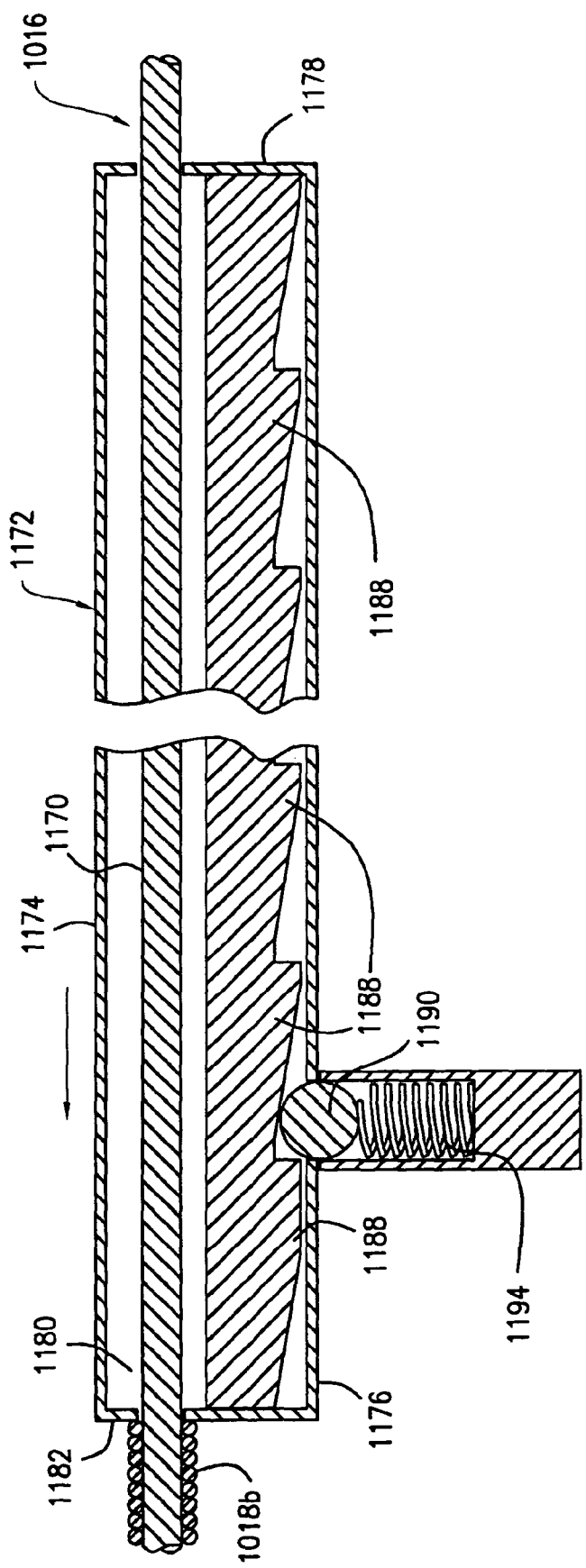
FIG. 18 is a cross-sectional view of the multi-feed mechanism shown in FIG. 17.

Now referring to FIGS. 16-18, a plunger 1172 is movably positioned in the casing 1012 for advancing the array of the suture anchoring devices 1018 axially forward subsequent to the performance of each suture anchoring operation. The plunger 1172, which has a tubular body 1174, a distal end 1176 and a proximal end 1178, is movably mounted on the support rod 1016 and is movably positioned in the bore 1056 of the pilot guide tube 1050. In this regard, a bore 1180 extends through the tubular body 1174 of the plunger 1172 for receiving the rigid body 1170 of the support rod 1016 therethrough. The distal end 1176 of the plunger 1172 is provided with a substantially cylindrical wall 1182 for engaging the suture anchoring device 1018b positioned at the rear (i.e., proximal) end of the array of the suture anchoring devices 1018. A handle 1184 projects from the tubular body 1174. More particularly, the handle 1184 extends laterally outwardly through the casing 1012 (see FIG. 13). An axially oriented slot 1186 (see FIG. 13) is formed in the casing 1012 for permitting axial movement of the handle 1184. Because the handle 1184 is fixedly attached to the plunger 1172, the plunger 1172 is movable in the axial direction in response to the movement of the handle 1184.

With reference to FIGS. 17 and 18, the plunger 1172 is equipped with ratchet-type teeth 1188 along a lower surface thereof. A spring-loaded ball or pin 1190 (see FIGS. 16 and 18) is mounted in the casing 1012 such that it engages one of the teeth 1188 of the plunger 1172. The ball 1190 is movably positioned in a hole 1192 formed in the casing 1012. A spring 1194 is mounted the hole 1192 so as to urge the ball 1190 against the plunger 1172. Each of the teeth 1188 is sloped such that the ball 1190 permits the plunger 1172 to move axially forward, while inhibiting same from moving axially rearward. Due to the constant engagement between the ball 1190 and the teeth 1188, the plunger 1172 is adapted to move forward by one tooth at a time. More particularly, each of the teeth 1188 is sized and shaped such that when the plunger 1172 is moved axially forward by one tooth, the array of the suture anchoring devices 1018 is moved in the forward direction by a distance substantially identical to the length of a single suture anchoring device 1018, thereby positioning the suture anchoring device 1018a positioned at the forward end of the array of the suture anchoring devices 1018 in position to be deployed by the suture winding device 1010. In this manner, multiple suture winding operations can be performed with the use of the suture winding device 1010 without removing and/or replacing the support rod 1016 after the performance of each suture anchoring operation.

It should be noted that the multi-feed mechanism of the suture winding device 1010 can have numerous modifications and variations. For instance, the plunger 1172 can be advanced forward incrementally by actuating (i.e., pressing) a spring-loaded button located on the casing 1010. In addition, the plunger 1172 can be eliminated by providing the rigid body 1170 of the support rod 1016 with threads adapted for advancing suture anchoring devices mounted thereon in the axial direction. Alternatively, a structure having a helical construction can be positioned upon the threaded support rod 1016. When this structure is rotated, it advances forward so as to cause suture anchoring devices mounted on the support rod 1016 to move in the axially forward direction.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

We claim:

1. A device for use in surgical procedure to anchor a suture to a coiled helical member, said device comprising winding means for winding a suture around the helical member in a helical path such that the suture is attached to at least one turn of the helical member, said winding means including
    a winding tube rotatable around an axis, said winding tube including securing means for securing at least a portion of the suture thereto so as to cause the suture to wind about the helical member, said securing means including a groove formed in said winding tube that is sized and shaped so as to receive at least a portion of the suture therein, said groove being angled in a direction opposite to the direction of rotation of said winding tube during the winding of the suture around the coiled helical member, said winding tube further including a plurality of first screw threads formed thereon, and a first gear mounted thereon; and
    a casing that is sized and shaped so as to be gripped by the hand of a surgeon, said casing having
    a plurality of second screw threads mating with said first screw threads such that said winding tube is mounted to said casing and rotatable relative thereto and movable in an axial direction in response to its rotational movement,
    a first actuator movably mounted on said casing and adapted for manual activation by a surgeon, and
    a set of second gears, said first gear being engaged with one of said second gears, said first actuator being engaged with another of said second gears such that said first gear and hence said winding tube are rotatable relative to said casing in response to the movement of said first actuator.

2. A device in accordance with claim 1, further comprising supporting means for supporting the helical member during the winding of the suture around the helical member.

3. A device in accordance with claim 2, further comprising a guide tube mounted in said winding tube and rotatable relative thereto.

4. A device in accordance with claim 3, wherein said guide tube includes a coiled spiral member at an end thereof, said spiral member being sized and shaped so as to receive the helical member therein during the winding of the suture about the helical member.

5. A device in accordance with claim 4, wherein said guide tube is movable in said axial direction relative to said winding.

6. A device in accordance with claim 5, wherein said guide tube has an opening extending through said spiral member, said opening being sized and shaped so as to receive the helical member therein.

7. A device in accordance with claim 6, wherein said spiral member includes a plurality of lobes extending radially inwardly into said opening, said lobes forming a plurality of spaces positioned radially outwardly from said opening.

8. A device in accordance with claim 7, wherein said guide tube includes a plurality of third screw threads formed thereon, said casing including a plurality of fourth screw threads mating with said third screw threads such that said guide tube is movable in said axial direction in response to the rotational movement of said guide tube.

9. A device in accordance with claim 8, wherein said guide tube includes a third gear mounted thereon, said casing including a second actuator movably mounted on said casing and adapted for manual actuation by a surgeon, said casing including a set of fourth gears, said third gear being engaged with one of said fourth gears, said second actuator being engaged with another of said fourth gears such that said third gear and hence said guide tube are rotatable in response to the movement of said second actuator.

10. A device in accordance with claim 9, wherein said supporting means includes a support rod extending through said guide tube for positioning the helical member in said opening of said spiral member of said guide tube.

11. A device in accordance with claim 10, wherein said support rod includes a distal end sized and shaped so as to engage the helical member.

12. A device in accordance with claim 11, wherein said distal end of said support rod is sized and shaped so as to engage the helical member by a friction fit.

13. A device in accordance with claim 11, wherein said support rod is sized and shaped so as to support at least one additional helical member thereon.

14. A device in accordance with claim 13, further comprising advancing means for advancing the at least one additional helical member in said axial direction.

15. A device in accordance with claim 14, wherein said advancing means includes a plunger mounted on said support rod, said plunger being movable in said axial direction.

16. A device for use in a surgical procedure to anchor a suture to a coiled helical member, said device comprising winding means for winding the suture around the helical member in a helical path such that the suture is attached to at least one turn of the helical member;

supporting means for supporting the coiled helical member during the winding of the suture around the helical member; and guiding means for guiding the winding of the suture in the helical path, said guiding means including a guide tube having a coiled spiral member at an end thereof, said spiral member being sized and shaped so as to receive the helical member therein during the winding of the suture about the helical member.

17. A device in accordance with claim 16 further comprising a casing, said winding means being rotatably mounted to said casing.

18. A device in accordance with claim 17, wherein said casing is sized and shaped so as to be gripped by a hand of a surgeon.

19. A device in accordance with claim 18, wherein said winding means includes a winding tube rotatable about an axis, said winding tube being movable in an axial direction in response to its rotational movement.

20. A device in accordance with claim 19, wherein said winding tube includes securing means for securing at least one portion of the suture thereto so as to cause the suture to wind about the helical member.

21. A device in accordance with claim 20, wherein said securing means includes a groove formed in said winding tube and sized and shaped so as to receive at least one portion of the suture therein.

22. A device in accordance with claim 21, wherein said groove is angled in a direction opposite to the direction of rotation of said winding tube during the winding of the suture about the helical member.

23. A device in accordance with claim 22, wherein said winding tube includes a plurality of first screw threads formed thereon, said casing including a plurality of second screw threads mating with said first screw threads such that said winding tube is movable in said axial direction in response to its rotational movement.

24. A device in accordance with claim, 16 wherein said guide tube is movable in an axial direction relative to said winding means.

25. A device in accordance with claim, 16 wherein said supporting means comprises a support rod extending through said winding means for supporting the helical member in a fixed position relative to said winding means while said winding means winds the suture about the helical member.

26. A device in accordance with claim 25, wherein said support rod includes a distal end sized and shaped so as to engage the helical member by a friction fit.

27. A device in accordance with claim 25, wherein said support rod includes a distal end sized and shaped so as to engage a plurality of helical members.

28. A device for anchoring a cord to a coiled helical member, said device comprising winding means for winding a cord about the helical member in a helical path such that the cord is attached to at least one turn of the helical member, said winding means including a winding tube rotatable about an axis and movable in an axial direction in response to its rotational movement, said winding tube including securing means for securing at least a portion of the cord thereto so as to cause the cord to wind about the coiled helical member, said securing means including a groove formed in said winding tube that is sized and shaped so as to receive at least one portion of the cord therein, said groove being angled in a direction substantially opposite to the direction of rotation of said winding tube during the winding of the cord about the coiled helical member; and guiding means for guiding the winding of the cord in the helical path, said guiding means including a guide tube mounted in said winding tube and rotatable relative thereto, said guide tube including a coiled spiral member at an end thereof, said spiral member being sized and shaped so as to receive the helical member therein during the winding of the cord about the helical member.

29. A device in accordance with claim 28, wherein said guide tube is movable in said axial direction relative to said winding tube in response to the rotation of said guide tube.

30. A device in accordance with claim 29, further comprising a supporting means for supporting the helical member during the winding of the suture around the helical member, said supporting means including a support rod extending through said guide tube for positioning the helical member in said spiral member of said guide tube.

31. A device for anchoring a cord to a coiled helical member, said device comprising winding means for winding the cord around the helical member in a helical path such that the cord is attached to at least one turn of the helical member;

guiding means for guiding the winding of the cord in the helical path, said guiding means including a guide tube having a coiled spiral member at an end thereof, said spiral member being sized and shaped so as to receive the helical member therein during the winding of the cord about the helical member; and supporting means for supporting the helical member during the winding of the cord around the helical member, said supporting means including a support rod extending through said guide tube for positioning the helical member in said spiral member of said guide tube.

32. A device in accordance with claim 31 wherein said winding means includes a winding tube rotatable about an axis, said winding tube movable in an axial direction in response to its rotational movement.

33. A device in accordance with claim 32, wherein said winding tube includes securing means for securing at least one portion of the cord thereto so as to cause the cord to wind about the helical member, said securing means including a groove formed in said winding tube and sized and shaped so as to receive at least one portion of the cord therein, said groove being angled in a direction substantially opposite to the direction of rotation of said winding tube during the winding of the cord about the helical member.

34. A method of anchoring a suture used in a surgical procedure to a coiled helical member, comprising the steps of supporting the helical member relative to a winding tube; and attaching the suture to at least one turn of the helical member by moving said winding tube relative to the helical member such that the suture is wound about the helical member in a helical path.

35. A method in accordance with claim 34, wherein said supporting step includes the step of positioning the helical member in a coiled spiral member of a guide tube.

36. A method of anchoring a suture used in a surgical procedure to a coiled helical member, comprising the steps of supporting the helical member relative to a winding tube that is rotatable about an axis, said winding tube being movable in an axial direction in response to its rotational movement; and moving said winding tube relative to the helical member such that the suture is wound about the helical member in a helical path so as to attach the suture to at least one turn of the helical member.

37. A method in accordance with claim 36, wherein said supporting step includes the step of positioning the helical member in a coiled spiral member of a guide tube.

* * * * *